(12) United States Patent
Noguchi et al.

(10) Patent No.: US 10,245,130 B2
(45) Date of Patent: Apr. 2, 2019

(54) POLYMERIZATION APPARATUS FOR DENTAL TECHNIQUE

(71) Applicant: GC CORPORATION, Tokyo (JP)

(72) Inventors: Yukie Noguchi, Itabashi-ku (JP); Mitsuaki Takada, Itabashi-ku (JP)

(73) Assignee: GC CORPORATION, Bunkyo-ku, Tokyo (JP)

( * ) Notice: Subject to any disclaimer, the term of this patent is extended or adjusted under 35 U.S.C. 154(b) by 0 days.

(21) Appl. No.: 15/508,701

(22) PCT Filed: Sep. 8, 2015

(86) PCT No.: PCT/JP2015/075452
§ 371 (c)(1),
(2) Date: Mar. 3, 2017

(87) PCT Pub. No.: WO2016/039332
PCT Pub. Date: Mar. 17, 2016

(65) Prior Publication Data
US 2017/0252138 A1    Sep. 7, 2017

(30) Foreign Application Priority Data

Sep. 10, 2014 (JP) .................................. 2014-184141

(51) Int. Cl.
*A61C 13/15* (2006.01)
*A61C 1/00* (2006.01)
(Continued)

(52) U.S. Cl.
CPC .......... *A61C 19/003* (2013.01); *A61C 1/0015* (2013.01); *A61C 13/0006* (2013.01); *A61C 13/12* (2013.01)

(58) Field of Classification Search
None
See application file for complete search history.

(56) References Cited

U.S. PATENT DOCUMENTS

2008/0136356 A1* 6/2008 Zampini ............ G06Q 30/0241
                                                    315/308
2013/0017124 A1* 1/2013 Noguchi ............. A61C 19/003
                                                    422/131
(Continued)

FOREIGN PATENT DOCUMENTS

CN    203169336 U    9/2013
JP    3-237973 A    10/1991
(Continued)

OTHER PUBLICATIONS

International Search Report of PCT/JP2015/075452, dated Nov. 24, 2015. [PCT/ISA/210].

*Primary Examiner* — Andrew Smyth
(74) *Attorney, Agent, or Firm* — Sughrue Mion, PLLC

(57) ABSTRACT

An object is to provide a polymerization apparatus for dental technique with which both of preliminary polymerization and final polymerization can be carried out by one apparatus. The apparatus includes a plurality of light sources whose light axes run at least in two directions; a cover that covers the light sources, forms a polymerization space inside thereof and switches a formation and closure of an opening that communicates inside and outside the polymerization space; a sensor that detects the formation and closure of the opening by the cover; a controller that receives signals from the sensor, and based on the formation and closure of the opening, turns on some of the light sources having two or more directions of light axis with the opening closed, and turns on some of the light sources having fewer directions of light axis than with the opening closed, with the opening open.

11 Claims, 18 Drawing Sheets

(51) Int. Cl.
*A61C 13/00* (2006.01)
*A61C 13/12* (2006.01)

(56) References Cited

U.S. PATENT DOCUMENTS

2013/0050984 A1* 2/2013 Van Beek ............... F25D 27/00
362/92
2013/0062535 A1 3/2013 Park et al.

FOREIGN PATENT DOCUMENTS

| JP | 5-95512 U | 12/1993 |
| JP | 6-61213 U | 8/1994 |
| JP | 2013-17616 A | 1/2013 |
| JP | 2014-226209 A | 12/2014 |
| JP | 2014-226210 A | 12/2014 |

* cited by examiner

POLYMERIZATION APPARATUS FOR DENTAL TECHNIQUE

CROSS REFERENCE TO RELATED APPLICATIONS

This application is a National Stage of International Application No. PCT/JP2015/075452 filed Sep. 8, 2015, claiming priority based on Japanese Patent Application No. 2014-184141 filed Sep. 10, 2014, the contents of all of which are incorporated herein by reference in their entirety.

TECHNICAL FIELD

The present invention relates to polymerization apparatuses for dental technique for curing photo-curable materials used in manufacturing dental prostheses in the dental field, especially in the field of dental technique, and a method for controlling the polymerization apparatuses for dental technique.

BACKGROUND

In the dental field, especially in the field of dental technique, widely carried out is a method, in which a photo-curable material (may be referred to as "polymerization material") is used to form a shape before the photo-curable material is cured (may be referred to as "polymerization"), and after the shape is formed, the photo-curable material is irradiated with light to be cured, to settle the shape, in manufacturing a dental prosthesis such as tooth restorations and artificial teeth. Polymerization apparatuses are devices for irradiating the photo-curable material with light to cure it.

Normally, in manufacturing a dental prosthesis, used are a preliminary polymerization apparatus and a final polymerization apparatus.

The preliminary polymerization apparatus is used when the material is stacked, for curing part of the stacked material, in order to prevent the part of the stacked material from deforming during work. In preliminary polymerization with the preliminary polymerization apparatus, a person who manufactures the dental prosthesis holds a half-manufactured dental prosthesis in hand, and irradiates portions where irradiation is required with light. This makes it possible to carry out local polymerization easily in a short time (For example, Patent Literatures 1 and 2).

The final polymerization apparatus is used after the material is all stacked, for uniformly polymerizing the entirety of the material as a finalization. Normally, the half-manufactured dental prosthesis before polymerization is placed in a chamber (container), and a closed space is formed by closing a door (cover) and the like, thereafter the entirety of the dental prosthesis is irradiated with light. The dental prosthesis is irradiated with light for, though depending on the size and fineness of the dental prosthesis, several minutes, whereby a sure polymerization is carried out. In view of carrying out polymerization efficiently, the dental prosthesis before the polymerization may be placed on a rotating table, and the polymerization is carried out by irradiating the dental prosthesis with light with the rotating table rotating (for example, Patent Literature 3).

Patent Literature 4 discloses a polymerization apparatus in which a preliminary polymerization apparatus is removably arranged next to a final polymerization apparatus, for convenience.

CITATION LIST

Patent Literatures

Patent Literature 1: JP H3-237973 A
Patent Literature 2: JP H6-61213 U
Patent Literature 3: JP 2013-17616 A
Patent Literature 4: JP H5-95512 U

SUMMARY

Technical Problem

Conventionally, as described above, a final polymerization apparatus and a preliminary polymerization apparatus are separately provided. The polymerization apparatus of Patent Literature 4 includes both apparatuses. However, the final polymerization apparatus and the preliminary polymerization apparatus are separately arranged, therefore it is not so different from a structure in which a final polymerization apparatus and a preliminary polymerization apparatus are separately provided.

Arranging two apparatuses for dental technique causes problems such as taking up of a large space. In addition, the two kinds of polymerization apparatuses cannot be simply combined to be one apparatus, because they are different in outer shape, irradiation range of light and intensity of light.

Considering the above problems, an object of the present invention is to provide a polymerization apparatus for dental technique with which both of preliminary polymerization and final polymerization can be carried out with one apparatus. Another object of the present invention is to provide a method for controlling such a polymerization apparatus for dental technique.

Solution to Problem

Hereinafter the present invention will be described.

An embodiment of the present invention is a polymerization apparatus for dental technique for curing a photo-curable material used for dental prostheses, including: a plurality of light sources whose light axes run at least in two directions; a cover that covers the light sources, forms a polymerization space inside thereof and switches a formation and closure of an opening that communicates inside and outside the polymerization space; a sensor that detects the formation and closure of the opening by the cover; a controller that receives signals from the sensor, and based on the formation and closure of the opening, turns on some of the light sources having two or more directions of light axis with the opening closed, and turns on some of the light sources having fewer directions of light axis than with the opening closed, with the opening open.

An embodiment of the present invention is a polymerization apparatus for dental technique for curing a photo-curable material used for dental prostheses, including: a plurality of light sources whose light axes run at least in two directions; a cover that covers the light sources, forms a polymerization space inside thereof and switches a formation and closure of an opening that communicates inside and outside the polymerization space; a sensor that detects the formation and closure of the opening by the cover; a controller that receives signals from the sensor, and based on the formation and closure of the opening, turns on some of the light sources having two or more directions of light axis with the opening closed, and turns on some of the light sources having fewer directions of light axis than with the opening closed, with the opening open; a switch that is arranged inside a space surrounded by the cover with the cover closed and that changes turning on and off of the light sources with the opening formed; and a switch that is arranged outside the space surrounded by the cover and that changes turning on and off of the light sources with the opening closed.

In the present invention, the light sources are able to light up with a high energy and a low energy, and the controller may carry out a calculation to make a decision to turn on the light sources with the low energy with the opening formed by the cover, and to make a decision to turn on the light sources with the high energy with the opening closed by the cover, with a depression of the switch arranged outside the space surrounded by the cover.

Advantageous Effects of Invention

According to the present invention, whether the cover has a posture with which an opening is formed or has a posture with which the opening is closed is judged to determine lighting of the lights. Thus, it is possible to carry out irradiation for preliminary polymerization with light and irradiation for final polymerization with light in one apparatus. Thus, it is possible to share lights between preliminary polymerization and final polymerization. In addition, it is possible to conserve space because there is no need to separately prepare a preliminary polymerization vessel and a final polymerization vessel.

DESCRIPTION OF EMBODIMENTS

Figure 1A:
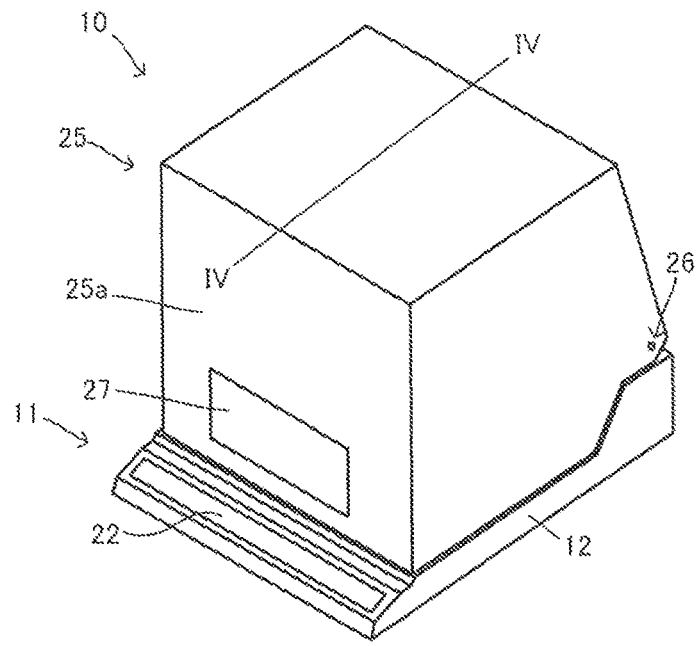
FIG. 1A is an outer perspective view of a polymerization apparatus for dental technique 10 with an opening closed.
Figure 1B:
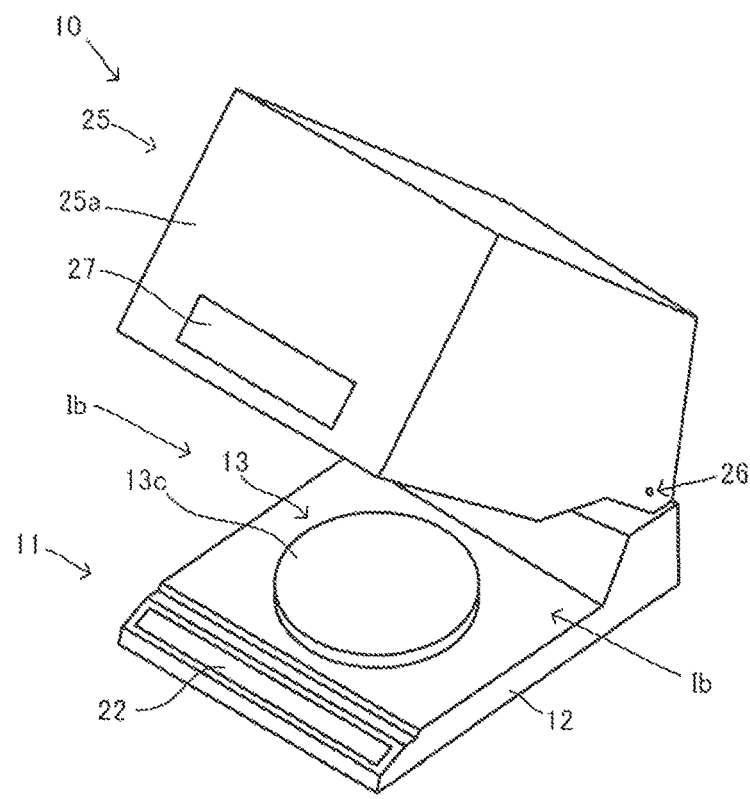
FIG. 1B is an outer perspective view of the polymerization apparatus for dental technique 10 with the opening formed.
Figure 2A:
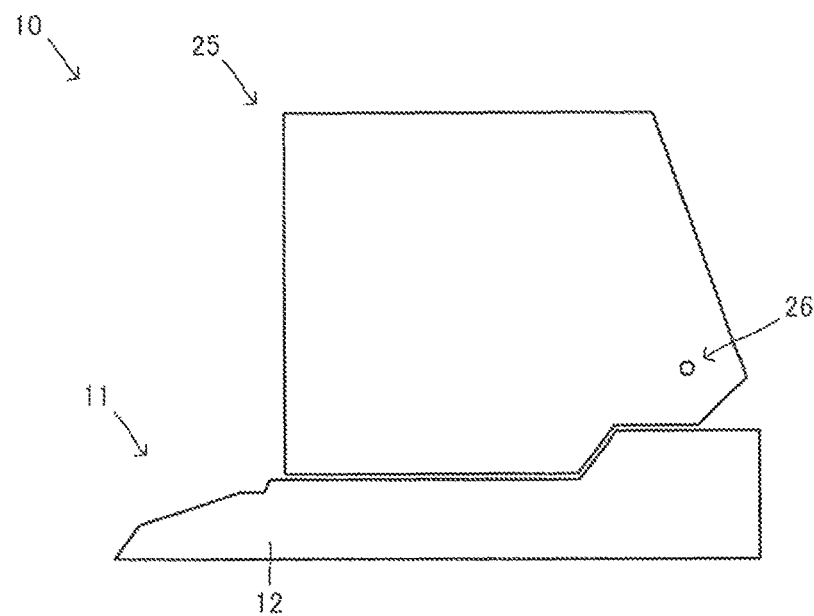
FIG. 2A is a side view of the polymerization apparatus for dental technique 10 with the opening closed.
Figure 2B:
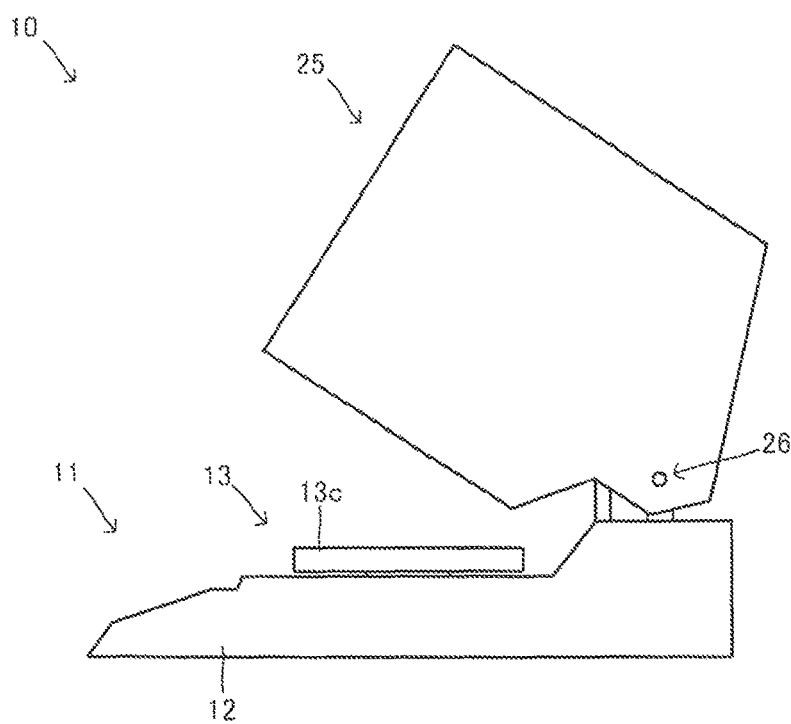
FIG. 2B is a side view of the polymerization apparatus for dental technique 10 with the opening formed.
Figure 3:
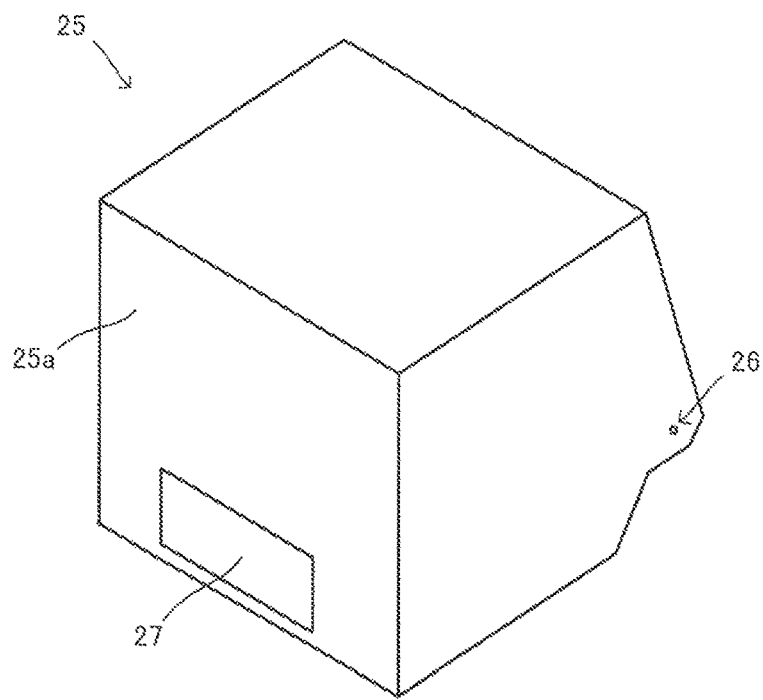
FIG. 3 is an exploded perspective view of the polymerization apparatus for dental technique 10.
Figure 3:
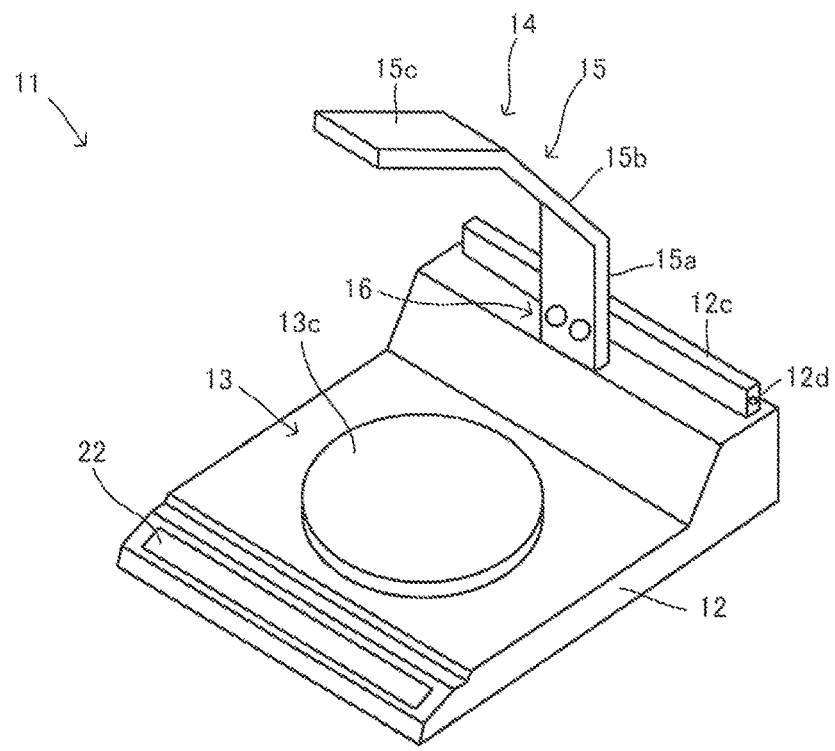
Figure 4:
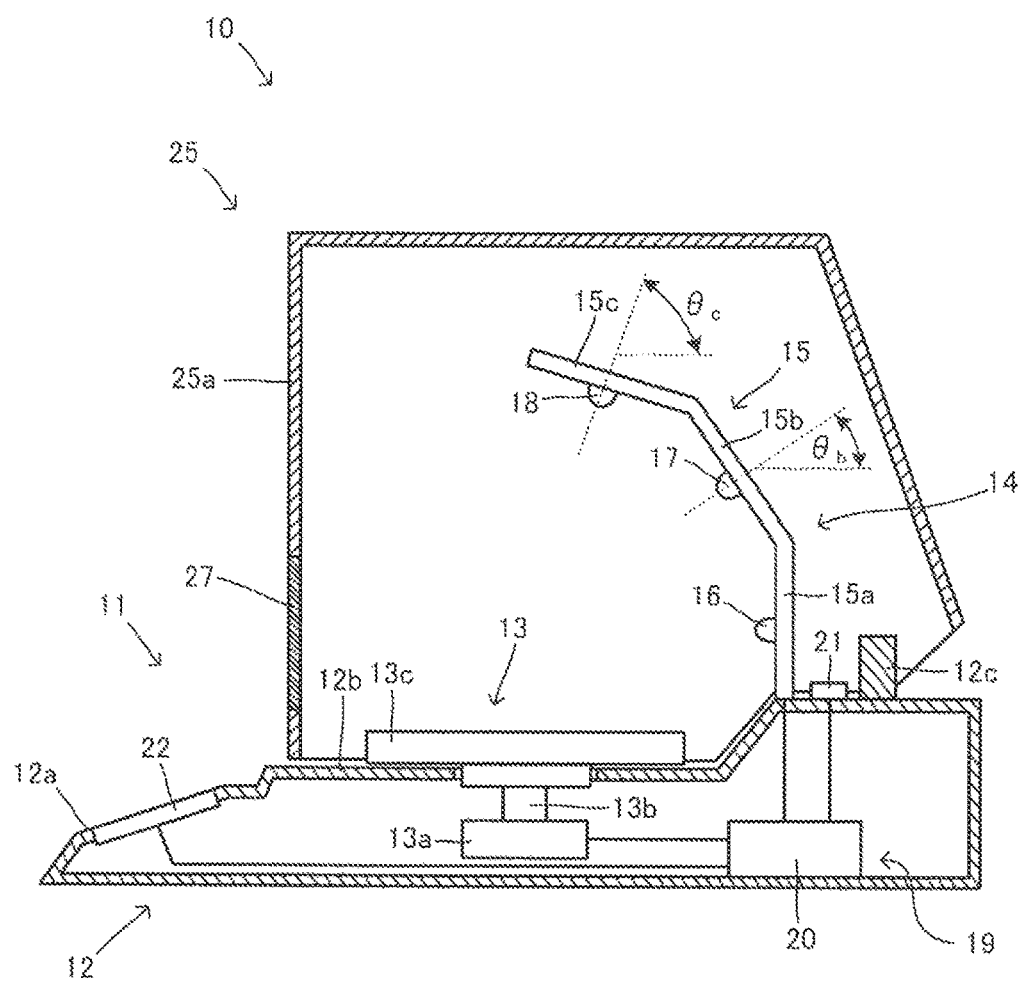
FIG. 4 is a cross-sectional view of the polymerization apparatus for dental technique 10 with the opening closed.
Figure 5:
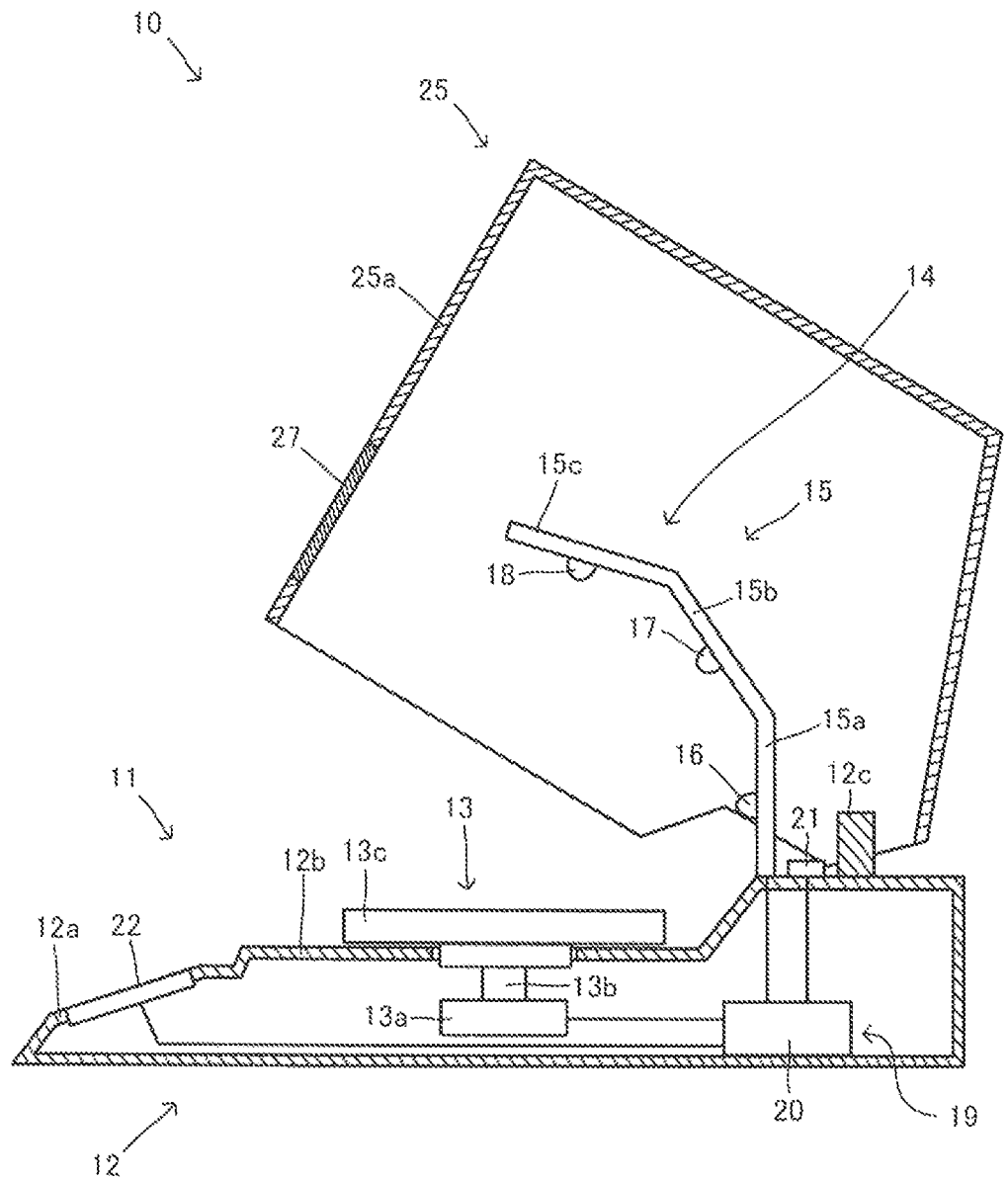
FIG. 5 is a cross-sectional view of the polymerization apparatus for dental technique 10 with the opening formed.

FIG. 1 is an outer perspective view of a polymerization apparatus 10 according to a first embodiment. FIG. 1A shows a posture with which a cover 25 is closed and an opening that communicates inside and outside the cover 25 is closed. FIG. 1B shows a posture with which the cover 25 is open and the opening that communicates inside and outside the cover 25 is formed. FIG. 2 is a side view of the polymerization apparatus for dental technique 10. FIG. 2A has the same posture as in FIG. 1A, and FIG. 2B has the same posture as in FIG. 1B. FIG. 3 is an exploded perspective view of the polymerization apparatus for dental technique 10, with the cover 25 separated. FIG. 4 is a cross-sectional view cutting the polymerization apparatus for dental technique 10 in the vertical direction along the line IV-IV shown in FIG. 1. Thus, FIG. 4 shows a cross section of the polymerization apparatus for dental technique 10 having a posture with which the cover 25 is closed and the opening that communicates inside and outside the cover 25 is closed. FIG. 5 shows a posture seen in the same viewpoint as in FIG. 4, with which the cover 25 is open and the opening that communicates inside and outside the cover 25 is open. In the cross-sectional views of FIGS. 4 and 5, at least part of the faces to be the cut surfaces is shown with hatched lines. Some cut surfaces are not shown with hatched lines to make the views easy to see.

As can be seen from these views, the polymerization apparatus for dental technique 10 includes a main body 11 and the cover 25. The main body 11 is a member in which main members of the polymerization apparatus for dental technique 10 are arranged. The cover 25 is arranged in a manner to cover part of the main body 11 from above. Polymerizations are carried out in a space surrounded by the main body 11 and the cover 25. The main body 11 includes a base 12, a rotating table 13, a light source member 14 and a controller 19. Hereinafter the structure of the polymerization apparatus for dental technique 10 will be described. The polymerization apparatus for dental technique 10 further includes known devices to function as a polymerization apparatus for dental technique (e.g. power source, electrical circuit and electrical wiring), which are not shown for easy understanding.

The base 12 is a member forming an outer shell of the main body 11. Most members of the polymerization apparatus for dental technique 10 are arranged inside or outside the base 12. Thus, the base 12 is of a hollow box shape, and the structural members of the polymerization apparatus for dental technique 10 can be arranged inside and outside the box shape.

In this embodiment, an operation panel arrangement part 12a, a polymerization space formation part 12b and a cover holding part 12c are arranged from one side to the other side, on a surface to be a top surface of the base 12.

The operation panel arrangement part 12a is a portion where an operation panel 22 of the controller 19 is to be arranged. The operation panel 22 is provided for a user, therefore it is preferable that the operation panel arrangement portion 12a be arranged on the user side (front face side, left side of sheet plane of FIG. 2A).

The polymerization space formation part 12b is a portion where the space for polymerization (polymerization space) is formed above. In this embodiment, the rotating table 13 is arranged there. A dental prosthesis 1 subject to polymerization is to be arranged on the rotating table 13 and irradiated with light (see FIG. 8).

The cover holding part 12c is a member to hold the cover 25 to the main body 11, including a shaft that makes the cover 25 turn when the cover 25 opens or closes to form and close an opening that communicates inside and outside the cover 25. Thus, in this embodiment, the cover holding part 12c includes a bearing 12d to accept a pivot shaft 26 provided to the cover 25. However, the means for enabling opening and closing of the cover 25 is not limited to this, and other known means can also be employed. For example, a hinge may be employed.

The rotating table 13 is a member arranged downward the polymerization space (preliminary polymerization zone and final polymerization zone) described later. The rotating table 13 includes a motor 13a, a rotating shaft 13b that can rotate by the motor 13a, and a mounting table 13c that rotates by the rotating shaft 13b. The dental prosthesis 1 is put on the rotating table 13, especially in final polymerization, directly, or via a height adjuster 2 that is a member to adjust the height of the dental prosthesis 1 (see FIG. 8). Examples of such an adjuster include block-shaped or plate-shaped members of predetermined thickness, and structures provided to enable the mounting table 13c itself to move up and down. The structures to enable the mounting table 13 to move up and down are not particularly limited, and a configuration to enable the rotating shaft 13b that rotates the mounting table 13c to move up and down may be given.

The arrangement of the rotating table 13 to the base 12 is carried out as follows for example. That is, the motor 13a of the rotating table 13 is arranged inside the base 12, and the mounting table 13c is exposed from the polymerization space formation part 12b of the base 12. This makes it possible to rotate the dental prosthesis 1 disposed on the mounting table 13c in final polymerization, which enables a further uniform curing (polymerization).

The light source member 14 is a device to emit light to polymerize and cure resin used for the dental prosthesis. In this embodiment, the light source member 14 includes a base plate 15 and a plurality of light sources 16, 17 and 18 arranged on the base plate 15.

The base plate 15 is a plate-shaped member vertically arranged between the polymerization space formation part 12b and the cover holding part 12c of the base 12. The base plate 15 in this embodiment has a configuration that three pieces of 15a, 15b and 15c are connected in the order mentioned, and the adjacent pieces are angled to each other. As seen from FIGS. 4 and 5, the piece 15a arranged closest to the base 12 among the pieces is vertically arranged upward from the base 12. The pieces 15b and 15c are arranged in a manner that the piece 15b extends from the tip of the piece 15a and the piece 15c extends from the tip of the piece 15b. At this time, the pieces 15a, 15b and 15c are formed in a manner to be angled so as to cover the polymerization space formation part 12b of the base 12 from above. The degrees of the angles formed by the pieces are determined according to the directions of the light axes of light sources 16, 17 and 18 to run. The directions will be described in the explanation of the light sources later.

In this embodiment, the base plate is formed of a plurality of pieces arranged having angles to each other. However, the base plate can also be formed curving like an arc in a manner to cover the polymerization space formation part 12b from above in the same way. Any known structure can be applied to the arrangement of the light sources in a manner to cover the polymerization space formation part 12b like this. For example, Patent Literature 3 discloses a structure.

The light sources 16, 17 and 18 are arranged on the pieces 15a, 15b and 15c of the base plate 15, respectively. The light sources 16, 17 and 18 are positioned in such a manner that they can emit light on the polymerization space formation part 12b side. Thus, the light source 16, the light source 17 and the light source 18 are arranged in such a manner that their light axes are different from each other. That is, the polymerization apparatus for dental technique 10 is provided with a plurality of light sources different in irradiation direction (light axis) (whose light axes run at least in two directions). Here, "light axis" means a direction of light of the highest brightness among the brightness distribution of the light emitted from the light source. More specific explanation will be made below. The light sources do not have to be one for each of the pieces 15a, 15b and 15c, and a plurality of light source may be arranged for each piece.

Figure 8:
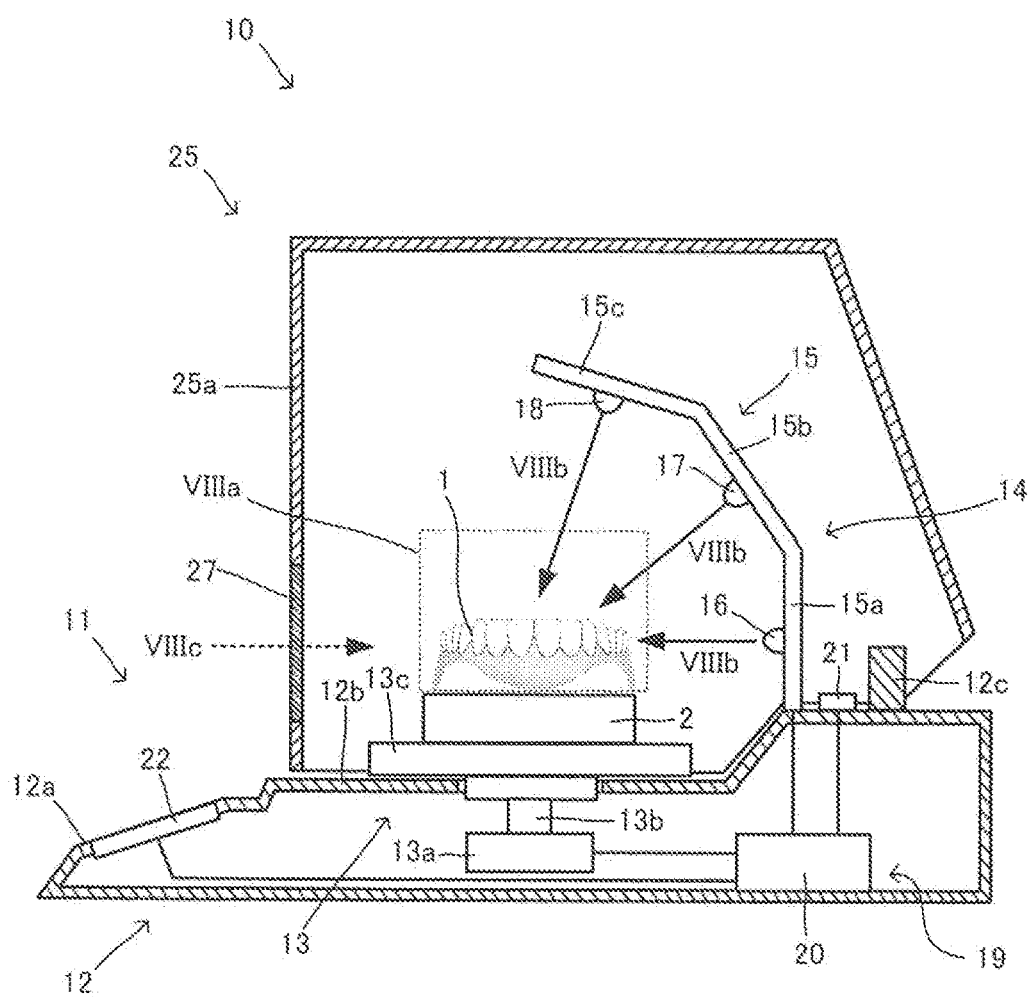
FIG. 8 is a cross-sectional view to explain a situation of final polymerization.

The light axis of the light source 16 arranged on the piece 15a is directed to the polymerization space formation part 12b almost horizontally (to the final polymerization zone in the polymerization space, VIIIa in FIG. 8). Preferably, the angle of the light axis relative to the level is in the range of ±10°. Here, the angle is a plus when the light axis is oriented downward, and a minus when the light axis is oriented upward. More preferably, the angle of the light source 16 is less than 0°. This makes it possible to irradiate undercut portions of a dental prosthesis of more complex shape with light.

The light axis of the light source 17 arranged on the piece 15b is oriented obliquely downward and directed to the polymerization space formation part 12b (final polymerization zone in the polymerization space, VIIIa in FIG. 8). Preferably, the angle of the light axis relative to the level (angle shown by θb in FIG. 4) is 45°±15°.

The light axis of the light source 18 arranged on the piece 15c is oriented downward and directed to the polymerization space formation part 12b (the final polymerization zone (VIIIa in FIG. 8) and preliminary polymerization zone (VIIa in FIG. 7) in the polymerization space). Preferably, the angle of the light axis relative to the level (angle shown by θc in FIG. 4) is 75°±15° and more preferably no less than 60° and less than 90°. By making the angle less than 90°, it is possible to form a large space in arranging a dental prosthesis on a right irradiation position in preliminary polymerization, therefore it is possible to secure easiness of work. Meanwhile, in final polymerization, it is possible to irradiate undercut portions of the dental prosthesis with light, with the rotation of the rotating table 13.

The light emitted from the light sources includes necessary wavelength for polymerization and curing of the polymerization material of the dental prosthesis. Normally, the wavelength region with which such a photo-curable material cures is in the range of from 300 nm to 520 nm. Thus, near ultraviolet, purple, blue and white light are preferable. Typical examples of the polymerization material include resin materials containing camphorquinone as a photo-curable material. The wavelength of the light at which this material starts polymerizing is around 470 nm.

Here, a light source that emits near ultraviolet means that the light source has a peak wavelength in the range of no less than 315 nm and less than 380 nm. A light source that emits purple light means that the light source has a peak wavelength in the range of no less than 380 nm and less than 430. A light source that emits blue light means that the light source has a peak wavelength in the range of no less than 430 nm and less than 520 nm.

The arrangement of the light sources of near ultraviolet, purple, blue and white is not particularly limited. One kind from them may be arranged, and two or more kinds from them may also be arranged. In this embodiment, as a part is shown in FIG. 3, different kinds of light sources may be arranged on the pieces 15a, 15b and 15c of the base plate 15. For example, a purple light source and a blue light source may be arranged on each of the pieces 15a, 15b and 15c.

The number of the light sources of same kind to be arranged is not particularly limited either, and may be one and may be two or more.

The kind and number of the light sources to be arranged may be the same or different from each other in the pieces 15a, 15b and 15c of the base plate 15. However, by making the number and kind of the light sources for each of the pieces 15a, 15b and 15c same, it is possible to inhibit uneven irradiation of light resulting from the directions of lights especially in final polymerization, and it is also possible to communize the members to improve the productivity.

The light sources 16, 17 and 18 may be any kind of light source such as xenon lamp and LED. In view of wavelength property of emitted light, life-span of light source, power consumption etc., LEDs are preferably used.

The controller 19 is a means to control each member provided to the polymerization apparatus for dental technique 10 to exert predetermined functions. In this embodiment, the controller 19 includes a control board 20, a cover detection sensor 21 and an operation panel 22.

The control board 20 receives signals from the cover detection sensor 21 and the operation panel 22 to carry out calculations, and transmits the results to the rotating table 13, the light source member 14 and the operation panel 22 to control them. Thus, the control board 20 has an electrical connection with the rotating table 13, the light source member 14, the cover detection sensor 21 and the operation panel 22. The control from the controller 19 will be specifically described later.

In this embodiment, the control board 20 is arranged inside the base 12 of the main body 11.

The control board 20 may be formed of an electrical circuit. The control board 20 includes, for example, a central processing unit (CPU) to actually carry out calculations, ROM in which programs are stored, and RAM used for a work area and storage of results, and is provided with an interface for the connection to each device. Known hardware may be used for them.

The cover detection sensor 21 is a sensor to detect the posture of the cover 25 to obtain information for judging whether the opening that communicates inside and outside the cover 25 is formed or closed. That is, the sensor 21 detects the posture of the cover 25 to transmit the information of the posture of the cover 25 to the control board 20. The control board 20 judges whether the opening that communicates inside and outside the cover 25 is formed or closed. Based on the result, the control board 20 carries out selection of light sources to turn on, calculation of lighting time, calculation to determine whether rotate or not rotate the rotating table 13, and the like, to control the light sources 16, 17 and 18, and the rotating table 13.

The sensor used here is not particularly limited, and examples thereof include micro switches and sensors to detect positions and rotations.

Figure 6A:
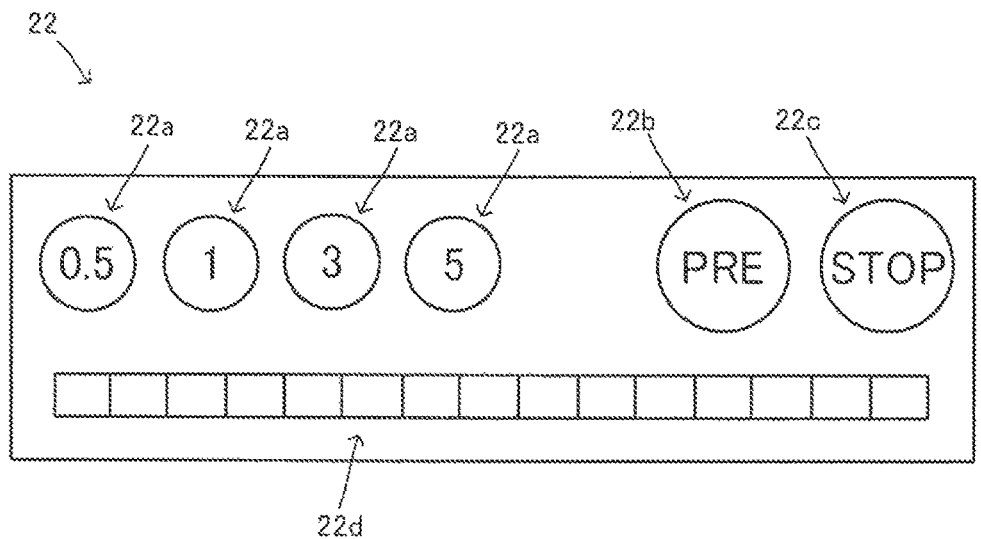
FIG. 6A is a view to explain an operation panel 22.

The operation panel 22 is a means for the user to input his/her intention, on which operating switches and various displays are arranged. This operation panel 22 is arranged outside the polymerization space surrounded by the cover 25. FIG. 6A shows one example of the operation panel 22. The operation panel 22 is provided with a lighting time setting switch for final polymerization 22a, a lighting start switch for preliminary polymerization 22b and a stop switch 22c. With the lighting time setting switch for final polymerization 22a, it is possible to set the time of 0.5 minute, 1 minute, 3 minutes and 5 minutes from the left side of FIG. 6A, and to turn on the light sources for final polymerization. By depressing the lighting start switch for preliminary polymerization 22b, the light sources for preliminary polymerization are turned on for a predetermined time.

The operation panel 22 is provided with a remaining time display part 22d to display the remaining time of the lighting of the light sources, at which the remaining time of the lighting of the light sources is displayed by a bar chart.

This makes it possible to transmit the input instructions of time and start of lighting as information, and the control board 20 selects light sources to turn on and calculate the lighting time to control the light sources 16, 17 and 18 and the rotating table 13.

Figure 6B:
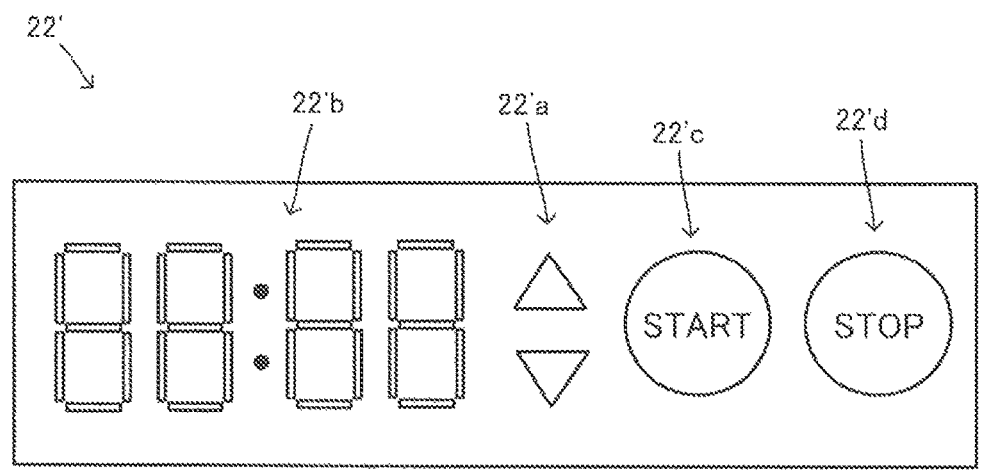
FIG. 6B is a view to explain an operation panel 22'.

Another example of the operation panel is shown in FIG. 6B. An operation panel 22' of another example can set the lighting time of the light source more precisely. That is, the operation panel 22' has a time setting switch 22'a to set the lighting time in seconds, and the set time is displayed on a time display part 22'b. The operation panel 22' is further provided with the start switch 22'c to start lighting and a stop switch 22'd to stop lighting.

Back to FIGS. 1 to 5, the cover 25 will be described. The cover 25 is a member to form, inside thereof, a polymerization space surrounding a dental prosthesis that includes materials subject to polymerization. In this embodiment, the cover 25 is formed in a box shape, one face of which is an opening portion that communicates inside and outside the cover. By arranging the opening portion in a manner to cover the top surface of the main body 11, a space surrounded by the cover 25 and the main body 11 is formed. At this time, as shown in FIG. 4, the mounting table 13c of the rotating table 13 and the light source member 14 are arranged inside the cover 25 in a manner to be covered by the cover 25.

The edge of the opening portion is formed in almost same shape as the shape of the top surface of the main body 11. This makes it possible to inhibit light emitted from the light sources 16, 17 and 18 from leaking.

As shown in FIG. 1A etc., the cover 25 is provided with a pivot shaft 26 at one end of the opening side, the pivot shaft 26 extending in the horizontal direction to the end side of the opening portion. This pivot shaft 26 is inserted in the bearing 12d of the cover holding part 12c provided to the base 12, whereby the cover 25 can turn around the pivot shaft 26. As can be seen from the comparison of FIGS. 1A and 1B, and comparison of FIGS. 2A and 2B, this makes it possible to turn up and down an end portion of the cover 25 on the opposite side of the pivot shaft 26, to form and close an opening that communicates inside and outside the cover 25.

Upon forming and closing the opening by turning the cover 25, a structure to keep any posture and a predetermined posture of the cover 25 (for example the posture to carry out preliminary polymerization) may be provided. With this structure, there is no need to hold the cover 25 by hand at a predetermined posture, and the convenience of the user may improve. The specific means for the structure is not particularly limited, and for example torque hinges and spring hinges may be used.

The opening formed by the cover 25 may be kept at any sizes. In this case as well, torque hinges and spring hinges may be used.

Here, the horizontal and vertical size of the opening formed by the cover 25 is preferably no less than 100 mm by no less than 100 mm. This makes it possible to secure a size with which the user can easily put in and out his/her hand with a dental technical material held in his/her hand.

The cover 25 is further provided with a light transmissive part 27 which is a portion where light pass through, provided on a wall 25a, the wall on the other side of the pivot shaft 26. The wall 25a is a wall of a cover 25, arranged in a manner to face the user of the polymerization apparatus for dental technique 10. This makes it possible for the user to visually observe inside the cover 25 through the light transmissive part 27.

The light transmissive part 27 is formed of a light transmissive plate fitted to an opening part provided to the wall 25a. The light transmissive plate is not particularly limited as long as it is transparent to such a degree that the inside of the cover 25 can be visually observed through the plate. Preferably, the light tramsmissive plate is configured to attenuate light in such a manner that the light of the peak wavelength of the light sources 16, 17 and 18 pass through the plate at a transmittance of no more than 20% (intercept no less than 80% of light). To this end, for example, a black filter that attenuates light over the whole wavelength, and a filter of orange that is the complementary color of the light sources 16, 17 and 18 may be used.

A magic mirror which transmits light of the peak wavelength of the light sources 16, 17 and 18 at a transmittance of no more than 20% and reflects at least part of the remaining 80% may also be used. This makes it possible to reduce glare from the light sources 16, 17 and 18, and to make the dental prosthesis easy to see, when the inside of the cover 25 is visually observed through the light transmissive part 27.

It is preferable that the light transmissive part 27 be arranged at a position where the portion under polymerization can be visually seen even with the cover 25 closed (FIG. 4, the posture with which the opening is closed) and even with the cover 25 open (FIG. 5, the posture with which the opening is formed).

It is preferable that the inner surface of the cover 25 be a surface having a high reflectance except the portion of the light transmissive part 27. This makes it possible to efficiently use the light emitted from the light sources 16, 17 and 18 for polymerization. The configuration of the reflection is not particularly limited, and the inner surface may be a regular reflection surface, and may be a diffuse reflection surface.

In this embodiment, shown is an example in which one end of the cover 25 turns up and down around the horizontally arranged pivot shaft 26, whereby the cover 25 opens and closes to form and close an opening that communicates inside and outside the cover. This makes it possible to form spaces not only at the front but also at the right and left (see Ib in FIG. 1B), through which hands can be put inside to carry out works, which improves workability.

The cover 25 is not limited to this, and the formation and closure of the opening that communicates inside and outside the cover may be carried out by a single or double sliding door that opens and closes the cover in the horizontal direction. In this case, the maximum opening degree of the cover may be limited to an opening degree for preliminary polymerization, and a structure to control (lock) the opening and closure of the door at the position to carry out preliminary polymerization may be provided. This makes it possible for the user to automatically obtain a necessary opening degree in preliminary polymerization, which improves convenience.

Next, a function of the polymerization apparatus for dental technique 10 will be explained with an explanation of a situation in which polymerization is carried out by the polymerization apparatus for dental technique 10. By this explanation, in addition to the above-described structure of the polymerization apparatus for dental technique 10, a structure to which the polymerization apparatus for dental technique 10 is desired to be provided, and an embodiment of the control by the controller 19 will be further understood.

Figure 7:
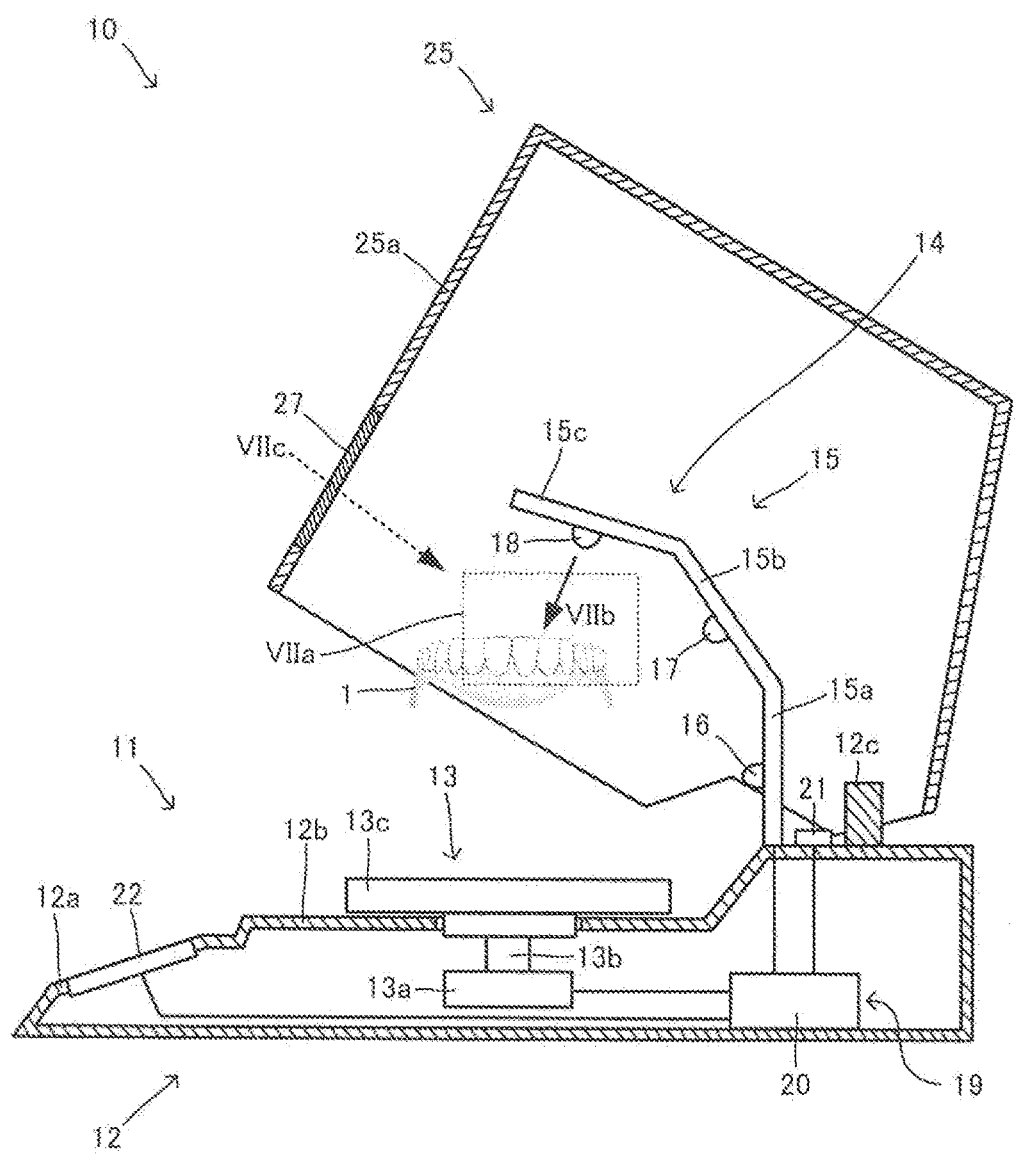
FIG. 7 is a cross-sectional view to explain a situation of preliminary polymerization.

A situation of preliminary polymerization will be described first. FIG. 7 shows a view to explanation. Preliminary polymerization is a work, in a process of manufacturing a dental prosthesis, to irradiate, with light, part of polymerization materials which are heaped and shaped, to polymerize the part. Thus, in preliminary polymerization, needed are to irradiate only necessary part of a dental prosthesis with light, and to irradiate the dental prosthesis with light with the user holding the dental prosthesis in hand, in order to precisely adjust the position to irradiate. In such a case, the user can use a preliminary polymerization mode of the polymerization apparatus for dental technique 10.

The preliminary polymerization mode automatically starts by the cover 25 taking a posture of opening (posture of preliminary polymerization) as shown in FIG. 7 to form an opening that communicates inside and outside the cover 25. This preliminary polymerization mode is set by the controller 19 as follows, when the cover 25 takes the posture of preliminary polymerization.

When the cover 25 takes the posture of preliminary polymerization, the cover detection sensor 21 provided to the controller 19 detects the posture of the cover 25, then transmits signals to the control board 20. The control board 20 that received the signals carries out calculations, to determine that the preliminary polymerization mode should be taken.

By the determination, the control board 20 regulates the rotation of the mounting table 13c of the rotating table 13 to control the mounting table 13c not to rotate. Further, the control board 20 regulates the light source member 14, in such a manner that at least one of the light sources whose light axis crosses the polymerization space formation part 12b can be turned on, and other light sources cannot be turned on. That is, the control board 20 regulates the light source member 14 in such a manner that some of the light sources, among the light sources having a plurality of light axes (two or more directions) light up such that the light axes thereof run only in part of directions (fewer directions than with the cover closed). In this embodiment, for example, the control board 20 regulates such that only the light source 18 can be turned on and the remaining light sources 16 and 17 cannot be turned on. As a result, a zone to be the irradiation range of the light source 18, which is inside the cover 25, becomes the preliminary polymerization zone VIIa as the polymerization space. At this time, the control board 20 sets the time to turn on the light source 18 and counts down (counts up) the lighting time.

It is preferable that the light sources to be turned on be light sources at positions where cannot be seen when the cover 25 takes the position of forming an opening. This makes it possible to improve safety.

Next, the user puts the dental prosthesis 1 subject to polymerization into the preliminary polymerization zone VIIa. This step is in preliminary polymerization. Thus, the dental prosthesis 1 is held by the users in hand directly or via a holder. The user, holding the dental prosthesis, depresses the lighting start switch for preliminary polymerization 22b of the operation panel 22 (see FIG. 6A). Whereby, only the light source 18 is turned on, the dental prosthesis 1 is irradiated with light as shown by VIIb in FIG. 7, and the light sources 16 and 17 remain turned off. At this time, the user can watch the dental prosthesis 1 through the light transmissive part 27 as shown by VIIc in FIG. 7, to proceed with the preliminary polymerization while confirming the position actually irradiated with light. Then, the light source 18 goes out when a predetermined time passes.

The light source 18 is preferably a blue LED, or blue and purple LEDs in order to efficiently carry out polymerization, because the light source 18 is used in preliminary polymerization as described.

The lighting of the light source 18 may be adjusted to be bright and dark, by adjusting energy for lighting. The lighting is carried out with a high energy when a polymerization is carried out efficiently and in a short time.

In this embodiment, the light source 18 is configured to light up only for a predetermined time period. However, in order to increase the flexibility of the time for preliminary polymerization, the light source 18 may be configured to light up when the switch is depressed and to go out when the switch is released. In this case, in order to improve the operability of the switch, a stick-shaped or plate-shaped switch or a non-contact sensor that detects the insertion of the dental prosthesis 1 may be provided at a portion surrounded by the cover 25 and the polymerization space formation part 12b of the base 12 when the cover 25 is closed, the portion being close to the preliminary polymerization zone VIIa. It is also possible to make a configuration in which the rotating table 13 itself doubles as the switch, to turn on the light source 18 by depression of the mounting table 13c and so on. It is also possible to arrange an operation panel having functions of the above-described operation panel 22 and 22' relating to preliminary polymerization, in a portion surrounded by the cover 25 and the polymerization space formation part 12b of the base 12 when the cover 25 is closed.

In addition, in order to make the position of the preliminary polymerization zone VIIa easy to understand, a means to be a mark may be provided. Examples thereof include laser light emitted along the light axis of the light source 18, and a mark on the light transmissive part 27.

In the above example, the dental prosthesis 1 is arranged in the preliminary polymerization zone VIIa before the lighting start switch for preliminary polymerization 22b of the operation panel 22 (see FIG. 6A) is depressed. However, adversely, dental prosthesis 1 may be arranged in the preliminary polymerization zone VIIa after the lighting start switch for preliminary polymerization 22b of the operation panel 22 is depressed. In this case, it is possible to control the lighting for example in such a manner that the light source 18 lights up approximately two seconds after the lighting start switch for preliminary polymerization switch 22b is depressed, or that the light source 18 lights up weakly (weak lighting) for that two seconds. This secures the time to arrange the dental prosthesis 1 in the preliminary polymerization zone VIIa.

When a plurality of light sources different in wavelength are used (e.g. blue and purple) for the light source 18, the light source 18 may be configured to select only either one of them (e.g. only blue, only purple) to turn on, depending on the polymerization material to use. This makes it possible to prevent unnecessary light sources from lighting up, to eliminate waste. The light source 18 may also be configured to switch the kind of LEDs to light up, so as to fit to the polymerization material to use.

It is possible to carry out a control to turn off all light sources by closing the cover 25 from the posture of preliminary polymerization (posture with which an opening is formed by the cover 25), and it is also possible to carry out a control to keep the light source 18 on even though the cover 25 closes. When the light source is kept on, it is possible to immediately restart the work of preliminary polymerization when the cover 25 openes again. It is also possible to set the light sources to go out after a predetermined time passes after the cover 25 closes.

It is also possible to make a configuration to reset the setting time (timer) of the operation panel when the cover 25 closes.

Next, a situation of final polymerization will be described. FIG. 8 shows a view for explanation. Final polymerization is a work, in a process of manufacturing a dental prosthesis, to finish heaping of all material and irradiate the entirety of the polymerization material with light to polymerize it and to finalize the work. Thus, in final polymerization, needed are to irradiate the entirety of the dental prosthesis with light as uniform as possible, and to complete the polymerization taking for a while. At this time, the user can use a final polymerization mode of the polymerization apparatus for dental technique 10.

The final polymerization mode automatically starts by the cover 25 taking a posture of closing (posture of final polymerization) as shown in FIG. 8, to close the opening that communicates inside and outside the cover 25. In this final polymerization mode, the following setting is made by the controller 19 when the cover 25 takes the posture of final polymerization.

When the cover 25 takes the posture of final polymerization, the cover detection sensor 21 provided to the controller 19 detects the posture of the cover 25 and transmits signals to the control board 20. The control board 20 that received the signals carries out calculations, and determines that the final polymerization mode should be taken.

By this determination, the control board 20 enables the rotation of the mounting table 13c of the rotating table 13, and controls the mounting table 13c to rotate. Further, the control board 20 controls the light source member 14 so that all light sources can light up. As a result, the irradiation zone of the light sources 16, 17 and 18 inside the cover 25 becomes the final polymerization zone VIIIa as a polymerization space.

The user places the dental prosthesis 1 subject to polymerization in the final polymerization zone VIIIa in advance. This process is in final polymerization, therefore the dental prosthesis 1 is put on the mounting table 13c directly or via the height adjuster 2. With the dental prosthesis 1 placed on the mounting table 13c, the user depresses the lighting start switch for final polymerization 22a of the operation panel 22 (see FIG. 6A). This makes the light sources 16, 17 and 18 turned on, and the dental prosthesis 1 is irradiated with light from a plurality of directions as shown by the allows VIIIb. At this time, the mounting table 13*c* is rotating. Thus, it is possible to carry out a uniform irradiation with light and uniform polymerization.

The user watches the dental prosthesis 1 through the light transmissive part 27 as shown in VIIIc in FIG. 8, whereby it is possible to proceed with final polymerization while confirming the position actually irradiated. The light sources 16, 17 and 18 go out when the time set by the lighting start switch for final polymerization 22*a* passes.

When a plurality of light sources different in wavelength (e.g. blue and purple) are used as the light sources 16, 17 and 18, a configuration may be taken in which only one kind of them can light up (e.g. lighting of only blue light sources, only purple light sources) according to the polymerization material used. This makes it possible to prevent unnecessary light sources from lighting up, to eliminate waste.

The lighting may be adjusted to be bright and dark by adjusting the energy for lighting. The lighting is carried out with a high energy when a polymerization is carried out efficiently and in a short time.

As described above, according to the polymerization apparatus for dental technique 10, it is possible to carry out preliminary polymerization and final polymerization in one apparatus. The switching of preliminary polymerization and final polymerization is automatically calculated from the posture of the cover 25, and their modes are set. Thus, the user can work without particularly confirming which mode is taken, therefore a high convenience is obtained. In addition, there is no need to provide two vessels of preliminary polymerization vessel and final polymerization vessel, thus it is possible to make the space to occupy small.

Whichever the mode is, the light from the light sources are prevented from directly going into the eyes of the user, thus it is possible to inhibit the work efficiency from degrading by glare. It is also possible, when the cover 25 is opened wider than the posture for preliminary polymerization, to detect the wide opening by the cover detection sensor 21, to control the light sources 16, 17 and 18 not to light up by the control board 20.

Figure 9:
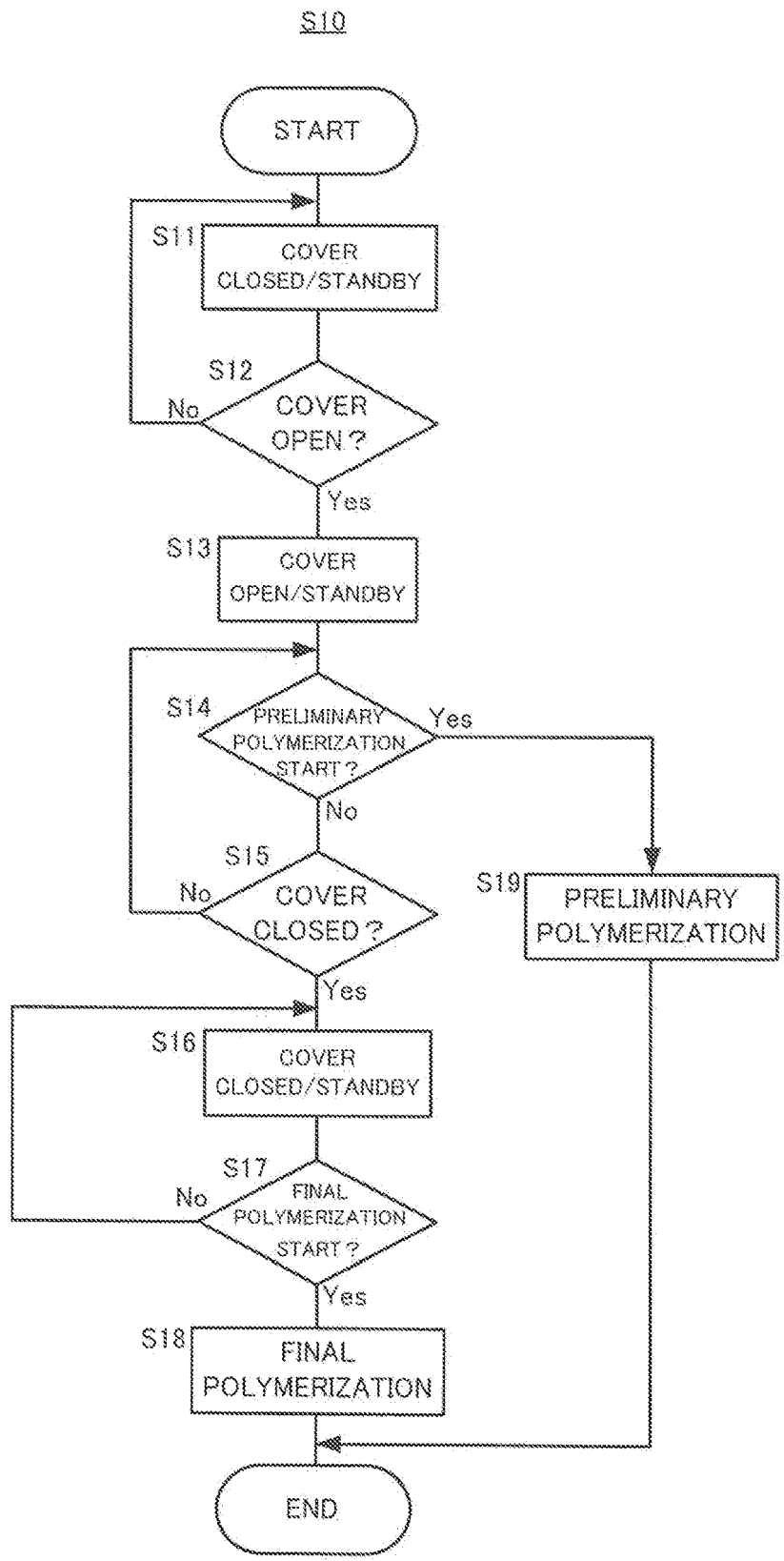
FIG. 9 is a flowchart of a control method S10 of the polymerization apparatus for dental technique.
Figure 10:
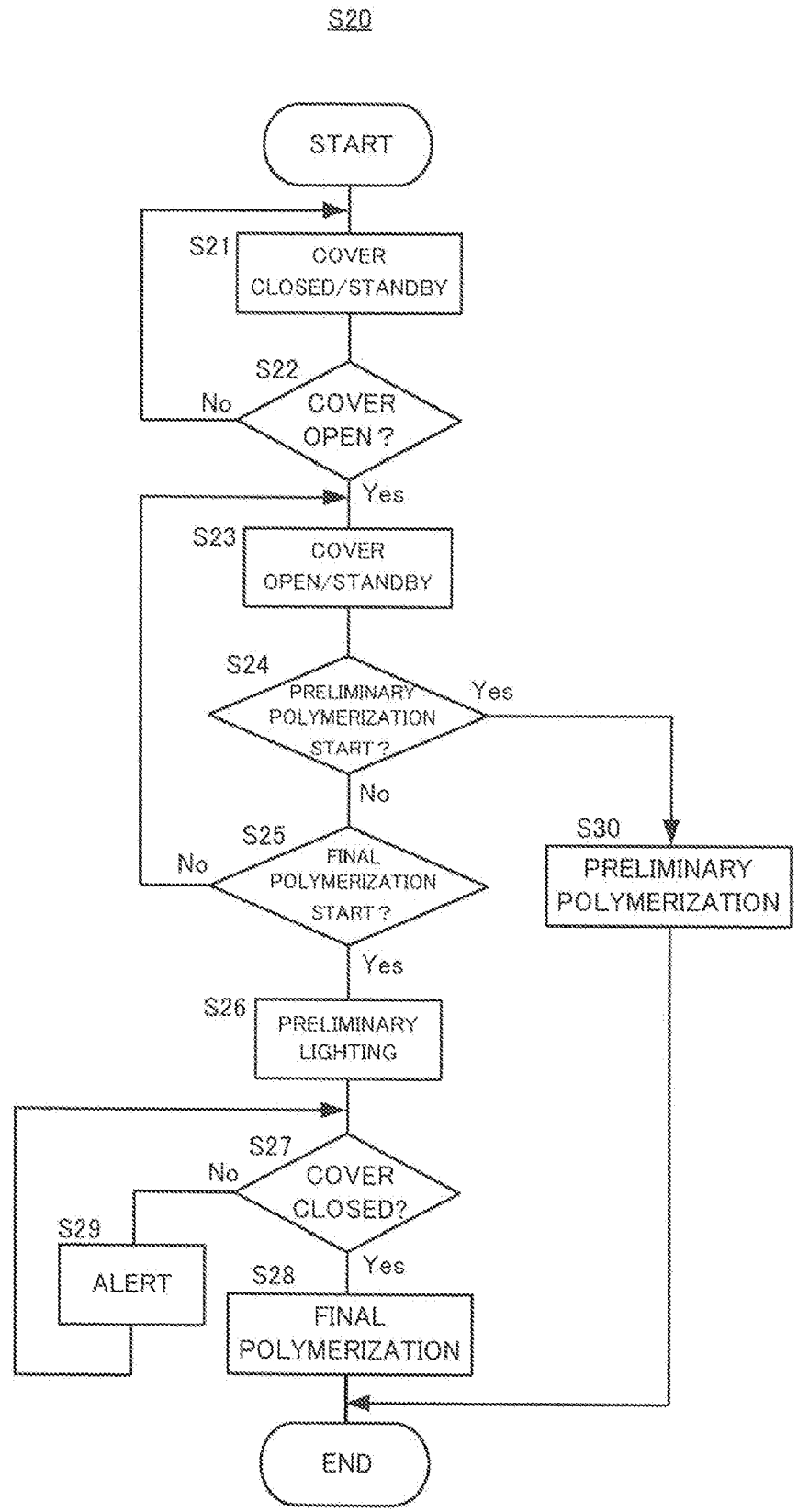
FIG. 10 is a flowchart of a control method S20 of the polymerization apparatus for dental technique.

Hereinafter, an example relating to a further specific control will be shown with reference to flowcharts. FIGS. 9 and 10 show the flowcharts. FIG. 9 is a flow chart of a control method S10 of a polymerization apparatus for dental technique according to one example. FIG. 10 is a flow chart of a control method S20 of a polymerization apparatus for dental technique according to another example.

As shown in FIG. 9, the control method S10 of a polymerization apparatus for dental technique includes steps S11 to S19. Each step is as follows.

S11 is a step in which the apparatus is in a standby condition with the cover closed (cover closed/standby step).

S12 is a step to judge whether the cover is open or not at the state of S11 (cover open judgment step). That is, in S12, whether the cover is opened by the user or not is judged. If the cover is not open, No is selected and S11 is kept. If the cover is open, S13 is carried out.

S13 is a step in which the apparatus is in a standby condition with the cover open (cover open/standby step).

S14 is a step to judge whether preliminary polymerization is started or not in the state of S13 (preliminary polymerization start judgment step), in which whether an instruction to start preliminary polymerization is made by the user or not is judged. When an instruction to start preliminary polymerization is made, Yes is selected, and preliminary polymerization starts at S19 (preliminary polymerization step). The step finishes by completion of the preliminary polymerization. When an instruction to start preliminary polymerization is not made, No is selected and S15 is carried out. The instruction to start preliminary polymerization can be made by the user depressing the lighting start switch for preliminary polymerization 22*b* of the operation panel 22, or when a switch is arranged inside the cover 25, by depressing the switch.

S15 is a step to judge whether the cover is closed or not (cover close judgment step). Assumed situations in which this step is made are when the user sets a polymerization subject (dental prosthesis) and closes the cover. If the cover is not closed, No is selected and the step returns to S14. When the cover is closed, Yes is selected, S16 is carried out and the apparatus stands ready with the cover closed (cover close/standby step).

S17 is a step to judge whether a final polymerization has started or not with the state of S16 (final polymerization start judgment step), in which whether an instruction to start final polymerization is made by the user or not is judged. When an instruction to start final polymerization is made, Yes is selected, and final polymerization starts at S18 (final polymerization step). The step finishes by the completion of the final polymerization. When an instruction to start final polymerization is not made, No is selected and S16 is kept. The instruction to start final polymerization can be made by the user closing the cover 25 or depressing the light starting switch 22'*c* (see FIG. 6B).

Next, the control method of a polymerization apparatus for dental technique S20 according to another example will be described. The control method of a polymerization apparatus for dental technique S20 includes steps S21 to S30 as shown in FIG. 10. Each step is as follows.

S21 is a step in which the apparatus is in a standby condition with the cover closed (cover closed/standby step).

S22 is a step to judge whether the cover is open or not in S21 (cover opening judgment step). That is, it is a step to judge whether the cover is opened by the user or not. When the cover is not open, No is selected and S21 is kept. If the cover is open, S23 is carried out.

S23 is a step in which the apparatus is in a standby condition with the cover open (cover open/standby step).

S24 is a step to judge whether preliminary polymerization is started or not in the state of S23 (preliminary polymerization start judgment step), in which whether an instruction to start preliminary polymerization is made or not by the user is judged. When an instruction to start preliminary polymerization is made, Yes is selected, and preliminary polymerization starts at S30 (preliminary polymerization step). The step finishes by completion of the preliminary polymerization. When an instruction to start preliminary polymerization is not made, No is selected and S25 is carried out. The instruction to start preliminary polymerization can be made by the user depressing the light starting switch 22*b* of the operation panel 22 for preliminary polymerization of the user, or, when a switch is arranged inside the cover 25, by depressing the switch.

S25 is a step to judge whether an instruction to start final polymerization is made or not (final polymerization start judgment step), in which an instruction to start final polymerization is made by the user or not is judged. When an instruction to start final polymerization is made, Yes is selected and S26 is carried out. When an instruction to start final polymerization is not made in S25, No is selected and the standby state of S23 is kept. The instruction to start final polymerization can be made by the user depressing the switch provided to the operation panels 22 and 22' and the like.

S26 is a step to tentatively light up the light sources (tentative lighting step). Here, the tentative lighting is a step of lighting up the light sources weakly, lighting up the light sources that are to be turned on in preliminary polymerization, and lighting up only part of the light sources. It means that S26 is a step of lighting up the light sources with a lower energy than in final polymerization. This step is made with consideration of convenience in confirming the position to be irradiated, by tentatively lighting the light sources with the cover open. The user can arrange a polymerization subject (dental prosthesis) while watching the state in the tentative light up. In this step, it is also possible to confirm there is no disconnecting or abnormality in the light sources.

When the light sources are turned on with a lower energy than in final polymerization, it is preferable that the lighting be carried out with a kind and intensity with which it is possible to directly see the light sources.

In view of the kind of the light sources, it is preferable that the light sources including a lot of ultraviolet be not turned on in the tentative lighting.

In view of irradiation intensity, it is preferable that the product of multiplication of the radiation illuminance and irradiation time be no more than 100 $J/m^2$. It is possible to set the lighting in such a manner that the light sources are forcibly turned off when the product becomes larger than the above value. For example, when 10 seconds of visual observation is assumed, the radiation illuminance will be no more than 10 $W/m^2$. It is also possible to set the time for tentative lighting by a timer with the operation panel within the time to the above forcible turning off, to limit the irradiation time.

S27 is a step to judge whether the cover is closed or not after S26 (cover closing judgment step S27). In this step, whether the cover is closed or not is judged before final polymerization, because final polymerization needs to be done with the cover closed. If the cover is not closed in S27, No is selected, and by an alert step S29, the apparatus alerts the user that the cover is not closed, with a sound or visual means, and S27 is kept. When the cover is closed, a step S28 (final polymerization step S28) is carried out and final polymerization is carried out. The step finishes by completion of the final polymerization.

It is also possible to make a setting that the tentative lighting or preliminary polymerization mode is set and timer temporary stops while the cover is open, when the cover 25 opens in final polymerization for some reason. This makes it possible for the user to remedy defects found in the final polymerization, and thereafter to restart the final polymerization. It is also possible to make a setting to turn off and reset the timer if the cover 25 opens in final polymerization for some reason. With this setting, a high convenience is obtained when interrupting the final polymerization.

Figure 11:
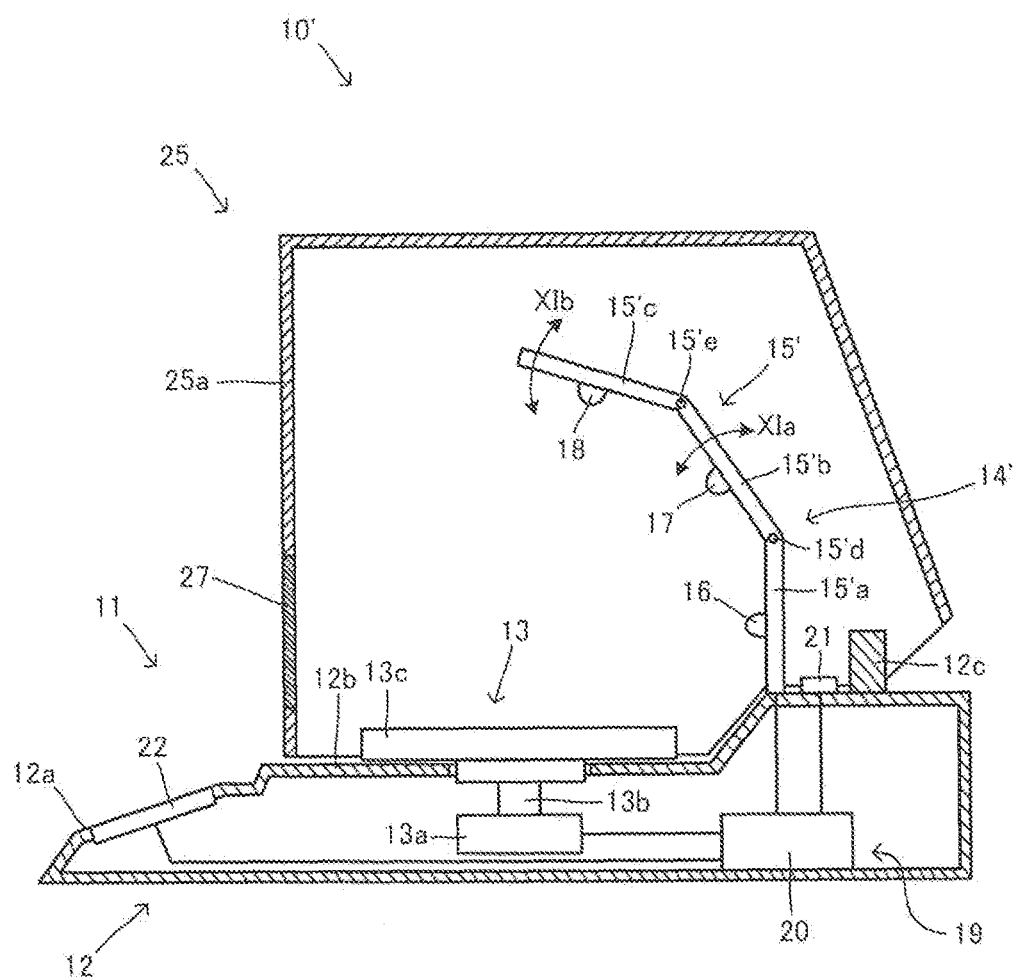
FIG. 11 is a cross-sectional view to explain a polymerization apparatus for dental technique 10'.

FIG. 11 is a view to explain a polymerization apparatus for dental technique 10' according to a modification example, a view seen from the same viewpoint as in FIG. 4. In this example, a light source member 14' is applied instead of the light source member 14 to the above-described polymerization apparatus for dental technique 10. Other members are the same as that of the polymerization apparatus for dental technique 10, therefore the same symbols are used and explanations thereof are omitted.

The light source member 14' is a device that emits light to polymerize and cure the polymerization material used for the dental prosthesis. In this embodiment, the light source member 14' includes a base plate 15', and the plurality of light sources 16, 17 and 18 arranged on the base plate 15'. The light sources 16, 17 and 18 are as described above.

The base plate 15' is a plate-shaped member vertically arranged between the polymerization space formation part 12b and the cover holding part 12c of the base 12. The base plate 15' in this embodiment includes three pieces 15'a, 15'b and 15'c connected to each other in the order mentioned. Adjacent pieces are turnably connected to each other. That is, as can be seen from FIG. 11, the piece 15'a arranged closest to the base 12 is vertically arranged from the base 12 upward. On the tip of the piece 15'a, the pieces 15'b is turnably connected by a pivot shaft 15'd. On the tip of the piece 15'b, the piece 15'c is turnably connected by a pivot shaft 15'e.

This makes it possible to change the inclination of the pieces 15'b and 15'c as shown by XIa and XIb in FIG. 11. Thus, it is possible to change the directions of the light axes of the light sources 17 and 18 arranged on the pieces 15'b and 15'c, and to adjust the directions of the light axes as necessary.

Figure 12:
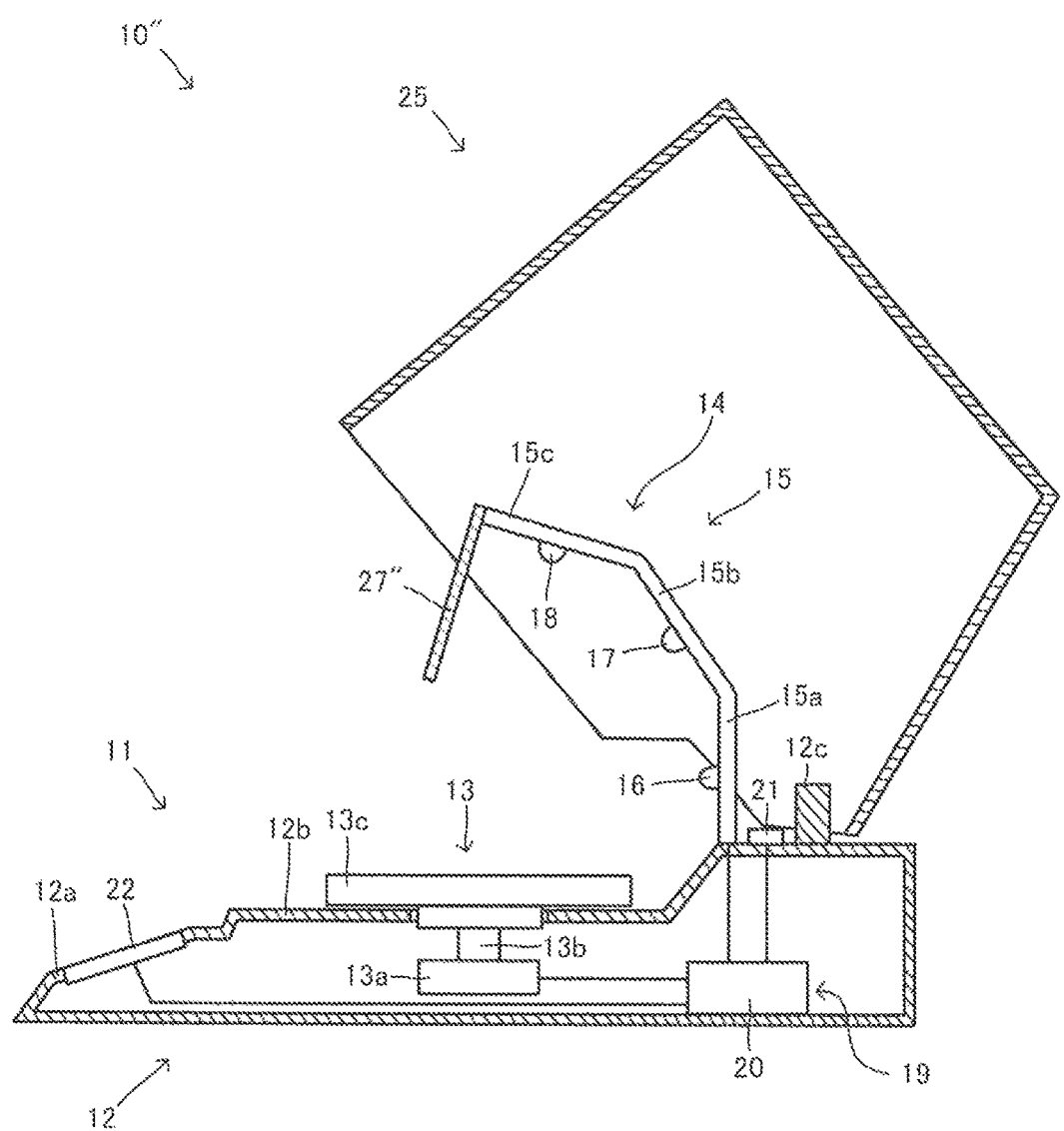
FIG. 12 is a cross-sectional view to explain a polymerization apparatus for dental technique 10"

FIG. 12 is a view to explain a polymerization apparatus for dental technique 10" according to another modification example, seen from the same viewpoint as in FIG. 5. In this example, a light transmissive part 27" is applied to the above-described polymerization apparatus for 10 instead of the light transmissive part 27. Other members are the same as in the polymerization apparatus for dental technique 10, therefore the same symbols are used and the explanations thereof are omitted.

The light transmissive part 27" in this example is arranged in a manner to hang down from the tip of the base plate 15 closest to the user side, and is provided in the polymerization space. The structure of the light transmissive part 27" itself is the same as the above-described light transmissive part 27.

According to the polymerization apparatus for dental technique 10" like this, it is possible to surely protect the eyes of the user, because the lights reach the user through the light transmissive part 27" even if the cover 25 is widely open. In addition, the light transmissive part 27" like this can also be a mark for the preliminary polymerization zone VIIa (see FIG. 7).

Figure 13:
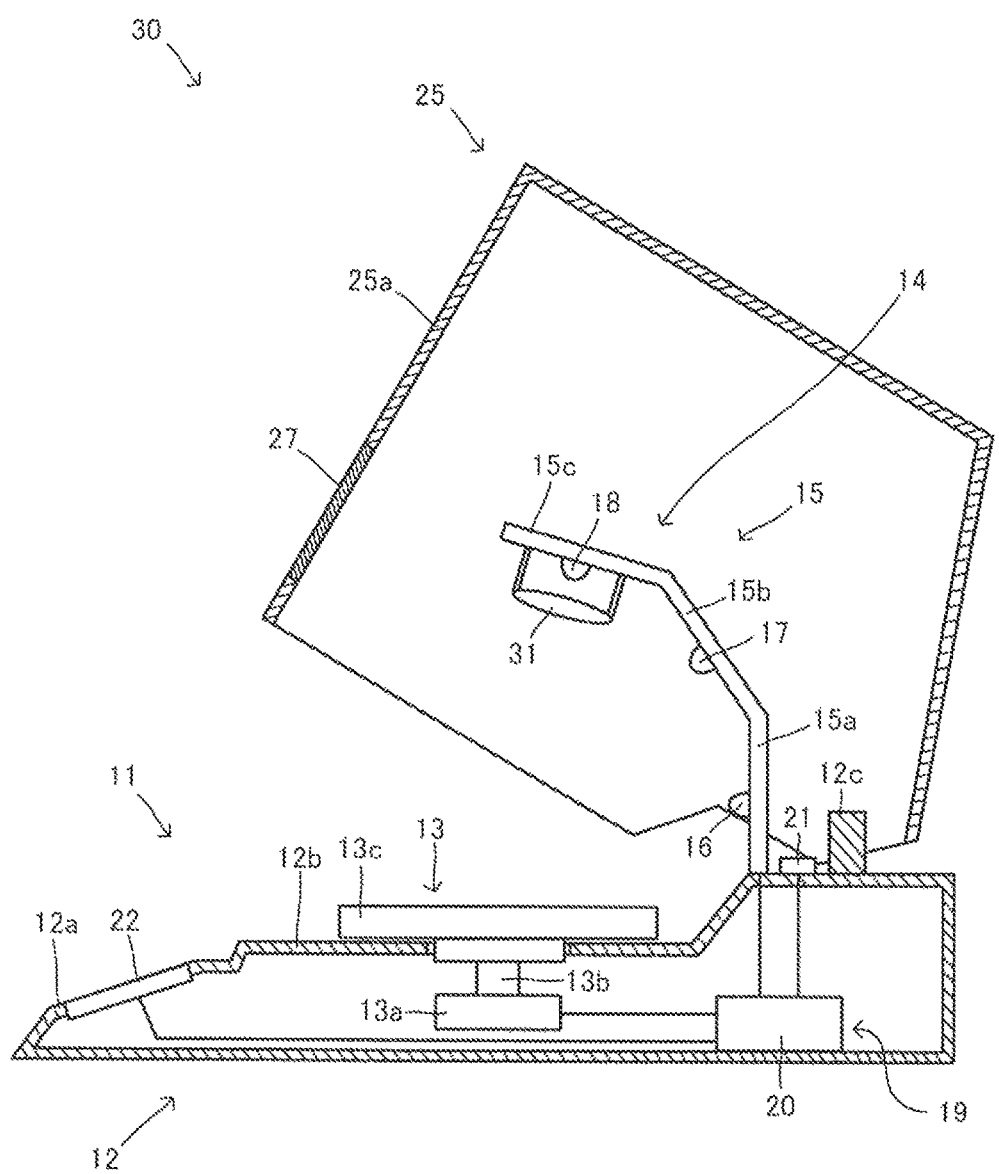
FIG. 13 is a cross-sectional view to explain a polymerization apparatus for dental technique 30.
Figure 14:
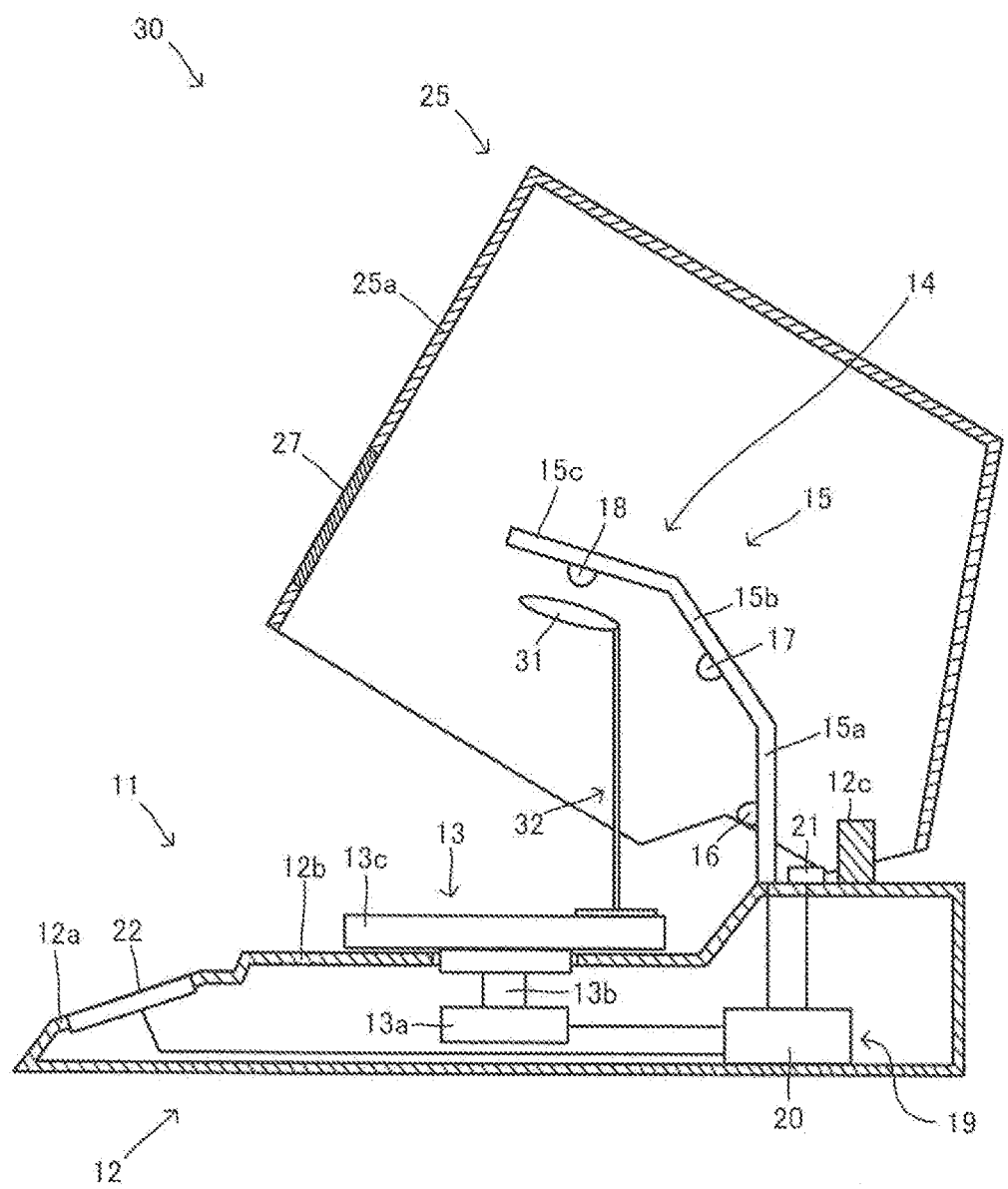
FIG. 14 is a cross-sectional view to explain another example of the polymerization apparatus for dental technique 30.

FIGS. 13 to 15 are views to explain a polymerization apparatus for dental technique 30 according to a second embodiment. Each view is seen from the same viewpoint as in FIG. 5. The polymerization apparatus for dental technique 30 is an example in which a collecting lens 31 is arranged on the light emitting side of the light source 18 of the polymerization apparatus for dental technique 10. Other members are the same as in the polymerization apparatus for dental technique 10, therefore the same symbols are used and the explanations thereof are omitted here.

Preliminary polymerization is for local polymerizations. Thus, in this embodiment, the collecting lens 31 is arranged on the light emitting side of the light source that lights up at the preliminary polymerization mode (in this example, the light source 18). This collects the light emitted from the light source 18 in preliminary polymerization to the collecting lends 31, and the dental prosthesis 1 is irradiated with the collected strong light. This makes it possible to efficiently carry out preliminary polymerization.

In final polymerization, desired is to irradiate the dental prosthesis 1 with light as wide range of the dental prosthesis 1 as possible. Thus, it is preferable that the collecting lens 31 be removed from the light emitting side of the light source 18, or be arranged in a manner not to collect light, in the final polymerization mode. Specific means for this configuration is not particularly limited, and examples thereof are shown in FIGS. 13, 14, 15A and 15B.

FIG. 13 shows an example in which the collecting lens 31 is directly attached to and removed from the piece 15c. In this example, the collecting lens 31 is manually attached to and removed from the piece 15c of the base plate 15 of the collecting lens 31 as necessary.

FIG. 14 shows an example in which a stand 32, on a tip of which the collecting lens 31 is arranged, is placed on the mounting table 13c, and the collecting lens 31 is arranged on the light emitting side of the light source 18. In this example as well, the stand 32 is manually placed on the mounting table 13c as necessary.

Figure 15A:
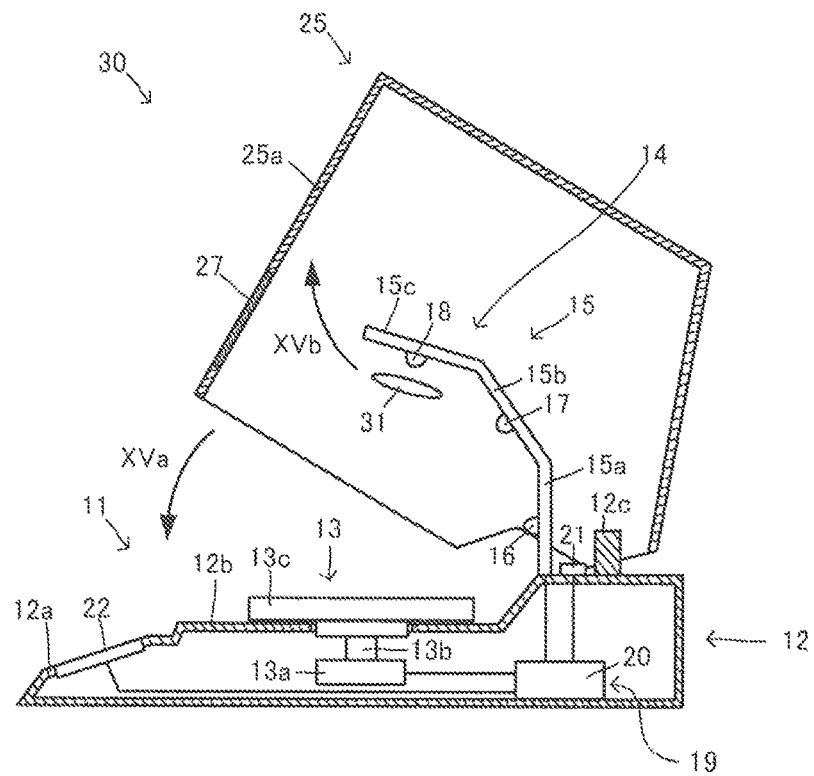
FIG. 15A is a cross-sectional view to explain another example of the polymerization apparatus for dental technique 30.

FIG. 15A shows an example in which the collecting lens 31 is held inside the cover 25, and the collecting lens 31 is automatically moved by a link structure, which is not shown. That is, as shown in FIG. 15A, in the posture of preliminary polymerization, the collecting lens 31 is arranged on the light emitting side of the light source 18 and collects light from the light source 18. However, when the cover 25 is closed as shown by the allow XVa in FIG. 5A (in the posture of final polymerization), the collecting lens 31 moves as shown by the arrow XVb in FIG. 15A, by means of the link structure, to be removed from the light emitting side of the light source 18.

Figure 15B:
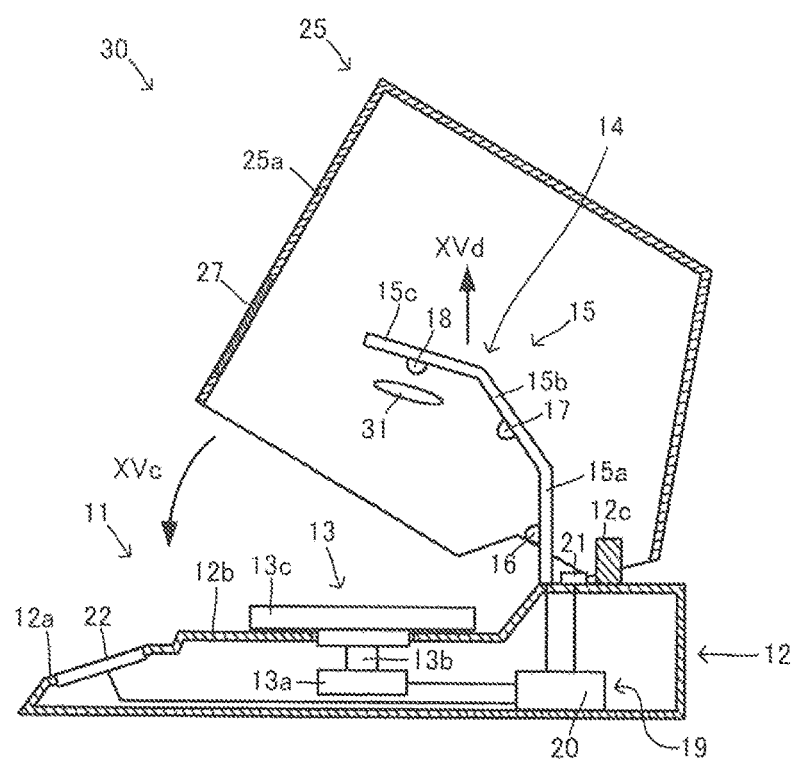
FIG. 15B is a cross-sectional view to explain still another example of the polymerization apparatus for dental technique 30.

FIG. 15B shows an example in which the relative distance between the collecting lens 31 and the light source 18 is changed, to change the degree of light collecting. That is, as shown in FIG. 15B, in the position of the preliminary polymerization mode, the collecting lens 31 and the light source 18 has such a distance that the collecting lens 31 collects light from the light source 18. However, when the cover 25 is closed as shown by the arrow XVc in FIG. 15B (in the posture of the final polymerization mode), the light source member 14 automatically moves up as shown by the arrow XVd in FIG. 15B, to change the distance between the collecting lens 31 and the light source 18. This makes it possible to stop the light collection. Here, an example in which the light source member 14 moves is described. However, the same action can be made by moving the collecting lens 31.

From the above configurations, it is possible to make local irradiation with a strong light in preliminary polymerization, to improve the efficiency of the preliminary polymerization. In this embodiment, the light from the light source 18 is collected in the preliminary polymerization mode and not collected in the final polymerization mode. However, in an opposite way, an embodiment in which a diffusing lens is arranged, used in the final polymerization mode and removed in the preliminary polymerization mode may also be taken. In this case, for example, the light source 18 may be made to have a property of collecting light, and a preliminary polymerization may be carried out by using the light source 18 with light collecting property in the preliminary polymerization mode, and in the final polymerization mode, the diffusing lens may be arranged to irradiate the dental prosthesis 1 at a wide range with light. For specific embodiments of the movement of the diffusing lens, the same way as in the above-described structure may be applied.

In view of controlling the direction of light, a reflector may also be attached to the light sources.

Figure 16:
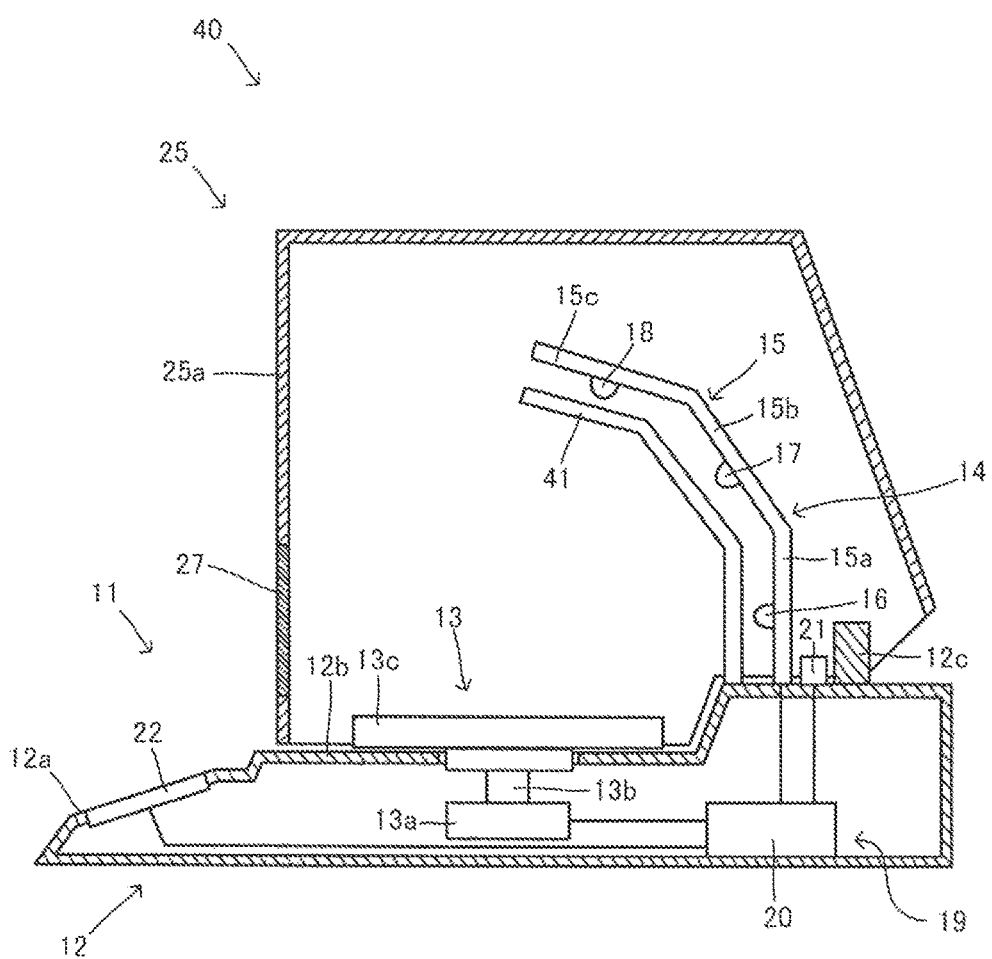
FIG. 16 is a cross-sectional view to explain a polymerization apparatus for dental technique 40.

FIG. 16 shows a view to explain a polymerization apparatus for dental technique 40 according to a third embodiment. This view is seen from the same viewpoint as in FIG. 4. In the polymerization apparatus for dental technique 40, a protective plate 41 is arranged on the light emitting side of the light source member 14 of the polymerization apparatus for dental technique 10. Other members are the same as in the polymerization apparatus for dental technique 10, therefore the same symbols are used and the explanations thereof are omitted here.

The protective plate 41 is a plate-like member arranged on the light emitting side of the light source member 14, arranged between the polymerization space and the light source member 14. The shape of the protective plate 41 is not particularly limited, and may be formed in a manner to conform to the shape of the base plate 15 of the light source member 14, as in this embodiment. The protective plate 41 is formed of a light transmissive member so as to let the light from the light sources 16, 17 and 18 pass through the protective plate 41. Only part of the protective plate through which the light emitted from the light sources 16, 17 and 18 pass may be transparent, or the whole part of the protective plate 41 may be transparent, because the protective plate 41 only has to let the light at least from the light sources 16, 17 and 18 pass through. With the protective plate 41, it is possible to protect the light sources 16, 17 and 18 from physical contact with dirt, the dental prosthesis 1 and the like.

The protective plate 41 is not particularly limited as long as it is a light transmissive member, and a lens may be provided thereto, for the purpose of diffusing or collecting light from the light sources 16, 17 and 18. The light transmissive member may be a resin member including two or more layers different in material between the light sources 16, 17 and 18 side and the opposite side thereto (polymerization space side). According to this, it is possible to replace only the layer on the side to be exposed to the polymerization space with a new one, when the layer gets dirty with the material to be polymerized, therefore it is possible to easily prevent the attenuation of light amount.

Figure 17:
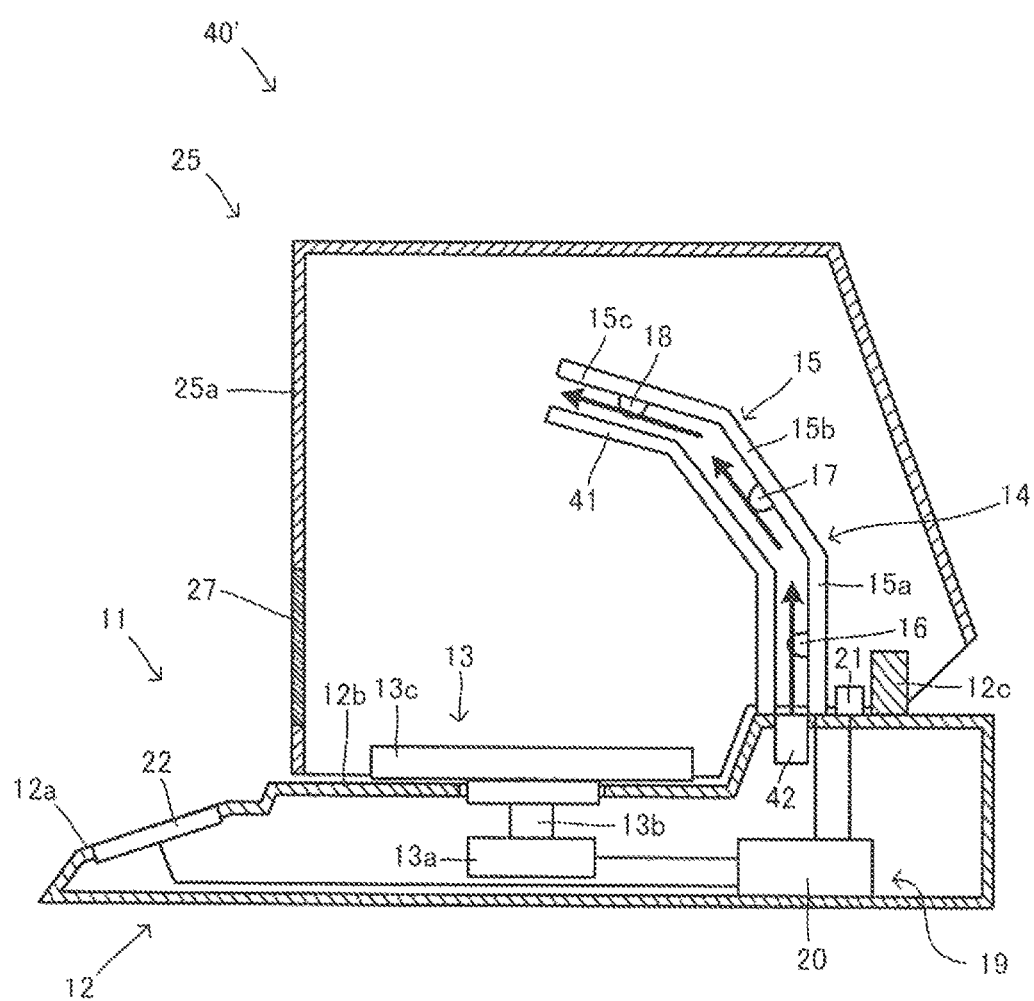
FIG. 17 is a cross-sectional view to explain a polymerization apparatus for dental technique 40'.
Figure 18:
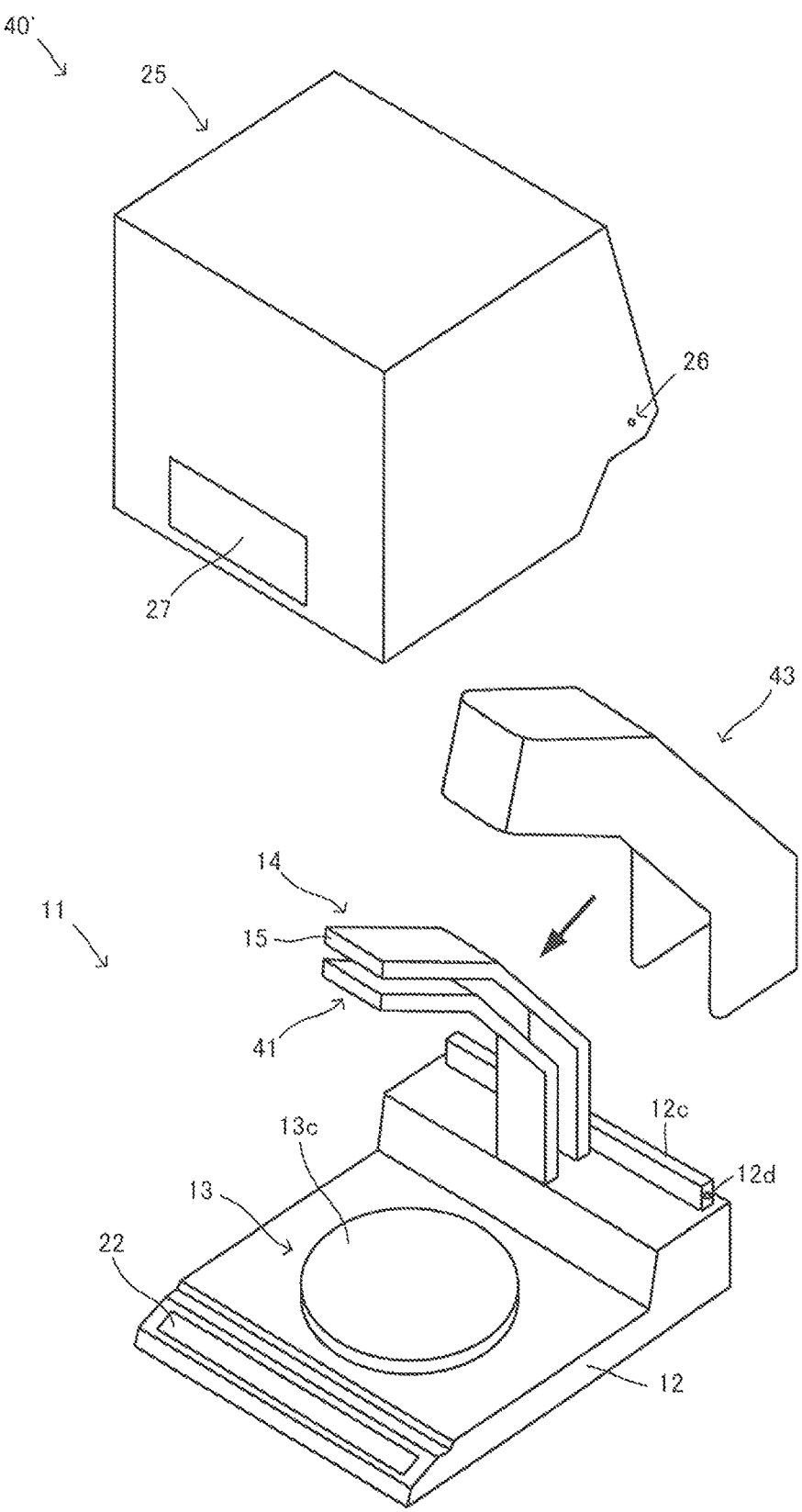
FIG. 18 is an exploded perspective view to explain another example of the polymerization apparatus for dental technique 40'.

FIG. 17 is a view to explain a polymerization apparatus for dental technique 40' according to a modification example of the polymerization apparatus for dental technique 40. In the polymerization apparatus for dental technique 40', a blower 42 is arranged to send air in between the base plate 15 of the light source member 14 and the protective plate 14, as shown by the straight arrows in FIG. 17. This makes it possible to cool down the light sources 16, 17 and 18, to improve the life spans of the light sources. At this time, as shown by the exploded perspective view of FIG. 18, a box-shaped cover 43 may be arranged in a manner to cover the surfaces of the light source member 14 and the protective plate 41 except their light emitting side surfaces, from a side of the light source member 14 opposite to the protective plate 41. This makes it possible to efficiently send air from the blower 42 in between the base plate 15 and the protective plate 41.

REFERENCES SIGN LIST 10, 30, 40 polymerization apparatus for dental technique
11 main body
  12 base
  13 rotating table
  14 light source member
  15 base plate
  16, 17, 18 light source
  19 controller
  20 control plate
  21 cover detection sensor
  22 operation panel
  25 cover
  26 pivot shaft
  27 light transmissive part

The invention claimed is:

1. A polymerization apparatus for dental technique for curing a photo-curable material used for dental prostheses, comprising:
a plurality of light sources whose light axes run at least in two directions;
a cover that covers the light sources, forms a polymerization space inside thereof and switches a formation and closure of an opening that communicates inside and outside the polymerization space;
a sensor that detects the formation and closure of the opening by the cover;
a controller that receives signals from the sensor, and based on the formation and closure of the opening, turns on, for a final polymerization, two or more of the light sources having two or more directions of a light axis with the opening closed when receiving signals from a switch, and turns on, for a preliminary polymerization, at least one of the light sources having fewer directions of the light axis than with the opening closed, with the opening open when receiving signals from the switch or from another switch that is different from the switch.

2. A polymerization apparatus for dental technique for curing a photo-curable material used for dental prostheses, comprising:
a plurality of light sources whose light axes run at least in two directions;
a cover that covers the light sources, forms a polymerization space inside thereof and switches a formation and closure of an opening that communicates inside and outside the polymerization space;
a sensor that detects the formation and closure of the opening by the cover;
a controller that receives signals from the sensor, and based on the formation and closure of the opening, turns on, for a final polymerization, two or more of the light sources having two or more directions of a light axis with the opening closed, and turns on, for a preliminary polymerization, at least one of the light sources having fewer directions of the light axis than with the opening closed, with the opening open;
a switch that is arranged inside a space surrounded by the cover with the cover closed and that changes turning on and off of the light sources with the opening formed; and
another switch that is arranged outside the space surrounded by the cover and that changes turning on and off of the light sources with the opening closed,
wherein
the turning on of the light sources by the controller is not carried out automatically by the formation of the opening.

3. The polymerization apparatus for dental technique according to claim 1, wherein the light sources are able to light up with a high energy and a low energy, and the controller carries out a calculation to make a decision to turn on the light sources with the low energy for the preliminary polymerization with the opening formed by the cover, and to make a decision to turn on the light sources with the high energy for the final polymerization with the opening closed by the cover, with a depression of the switch or the another switch.

4. The polymerization apparatus for dental technique according to claim 2, wherein the light sources are able to light up with a high energy and a low energy, and the controller carries out a calculation to make a decision to turn on the light sources with the low energy for the preliminary polymerization with the opening formed by the cover, and to make a decision to turn on the light sources with the high energy for the final polymerization with the opening closed by the cover, with a depression of the another switch arranged outside the space surrounded by the cover.

5. The polymerization apparatus for dental technique according to claim 1, wherein at least one of the light sources has a light axis in a direction of the opening.

6. The polymerization apparatus for dental technique according to claim 2, wherein at least one of the light sources has a light axis in a direction of the opening.

7. The polymerization apparatus for dental technique according to claim 5, wherein the controller turns on the light sources not having the light axis in the direction of the opening, when turning on, for the preliminary polymerization, at least one of the light sources having fewer directions of the light axis than with the opening closed.

8. The polymerization apparatus for dental technique according to claim 6, wherein the controller turns on the light sources not having the light axis in the direction of the opening, when turning on, for the preliminary polymerization, at least one of the light sources having fewer directions of the light axis than with the opening closed.

9. The polymerization apparatus for dental technique according to claim 1, further comprising a light transmissive plate that attenuates light with which the polymerization space can be visually observed when the preliminary polymerization is carried out with the opening formed by the cover.

10. The polymerization apparatus for dental technique according to claim 2, further comprising a light transmissive plate that attenuates light with which the polymerization space can be visually observed when the preliminary polymerization is carried out with the opening formed by the cover.

11. A polymerization apparatus for dental technique for curing a photo-curable material used for dental prostheses, comprising:
a plurality of light sources being able to light up with a high energy and a low energy;
a cover that covers the light sources, forms a polymerization space inside thereof and switches a formation and closure of an opening that communicates inside and outside the polymerization space;
a sensor that detects the formation and closure of the opening by the cover;
a light transmissive plate that attenuates light with which the polymerization space can be visually observed with the opening formed by the cover; and
a controller that makes a decision to turn on the light sources with the low energy for a preliminary polymerization with the opening formed by the cover, and makes a decision to turn on the light sources with the high energy for a final polymerization with the opening closed by the cover.

* * * * *